(12) United States Patent
Hayat et al.

(10) Patent No.: US 12,702,321 B2
(45) Date of Patent: Aug. 11, 2026

(54) SYSTEM AND METHOD OF SENSING CATHETERS LOCATION AND FORCE

(71) Applicant: BIOSENSE WEBSTER (ISRAEL) LTD., Yokneam (IL)

(72) Inventors: Nathanel Yehuda David Hayat, Petah Tivka (IL); Barry Neal Breen, Givat Zeev (IL); Avraham Cohen, Kiryat Bialik (IL); Daniel Zohar, Zichron Yakov (IL); Shemer Shmaryau Berkowitz, Binyamina (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 18/749,244

(22) Filed: Jun. 20, 2024

(65) Prior Publication Data

US 2025/0009247 A1 Jan. 9, 2025

Related U.S. Application Data

(60) Provisional application No. 63/523,440, filed on Jun. 27, 2023.

(51) Int. Cl.
*A61B 5/00* (2006.01)
*A61B 5/06* (2006.01)

(52) U.S. Cl.
CPC ........... *A61B 5/065* (2013.01); *A61B 5/6852* (2013.01); *A61B 2562/12* (2013.01)

(58) Field of Classification Search
CPC ... A61B 5/065; A61B 5/6852; A61B 2562/12; A61B 34/20; A61B 5/062;
(Continued)

(56) References Cited

U.S. PATENT DOCUMENTS 6,690,255 B2 2/2004 Caramela et al.
7,816,915 B2 * 10/2010 Susel .................... H01F 41/076 336/208

(Continued)

FOREIGN PATENT DOCUMENTS

EP 1315178 A1 5/2003
EP 2196143 A1 6/2010

(Continued)

OTHER PUBLICATIONS

European Search Report for corresponding EPA No. 24184690.6 dated Aug. 20, 2024.

(Continued)

*Primary Examiner* — Joel Lamprecht
(74) *Attorney, Agent, or Firm* — Clayton, McKay & Bailey, PC

(57) ABSTRACT

A position sensor for measuring signals indicative of location and/or orientation a catheter's distal end, and a method of fabrication thereof are disclosed. The position sensor includes a flexible circuit board (FCB) and at least three surface mount coil devices (SMD coils) arranged thereon for sensing different aspects of one or more magnetic fields, which are indicative of the location and/or orientation of the catheters distal end. The FCB is furnished at the sensor in folded/rolled state such that the magnetic flux axes of at least three of the SMD coils are not co-planar to thereby enable utilizing signals measured thereby determine the at least one of the orientation and location of the sensor relative to one or more magnetic field sources.

21 Claims, 10 Drawing Sheets

(58) Field of Classification Search
CPC ........ A61B 2034/2051; G01R 33/0005; G01R 33/0052; G01R 33/0206; G01R 33/028; H05K 1/189; A61M 25/0105; A61M 2025/0166; G01B 7/003; G01L 1/127
See application file for complete search history.

(56) References Cited

U.S. PATENT DOCUMENTS

| | | | | |
|---|---|---|---|---|
| 7,924,000 B2 * | 4/2011 | Susel | H01F 5/04 | |
| | | | 336/200 | |
| 8,535,308 B2 * | 9/2013 | Govari | A61B 1/00097 | |
| | | | 606/41 | |
| 8,900,229 B2 * | 12/2014 | Govari | A61B 5/06 | |
| | | | 606/41 | |
| 2020/0015693 A1 | 1/2020 | Beeckler | | |

FOREIGN PATENT DOCUMENTS

| | | |
|---|---|---|
| EP | 1806756 B1 | 8/2017 |
| EP | 4510154 A1 | 2/2025 |

OTHER PUBLICATIONS

Uchiyama S. et al., "Novel MEMS-based fabrication technology of micro solenoid-type inductor", Journal of Micromechanics and Microengineering, Institute of Physics Publishing, Bristol, GB, vol. 23, No. 11, Oct. 24, 2013, p. 114009.

* cited by examiner

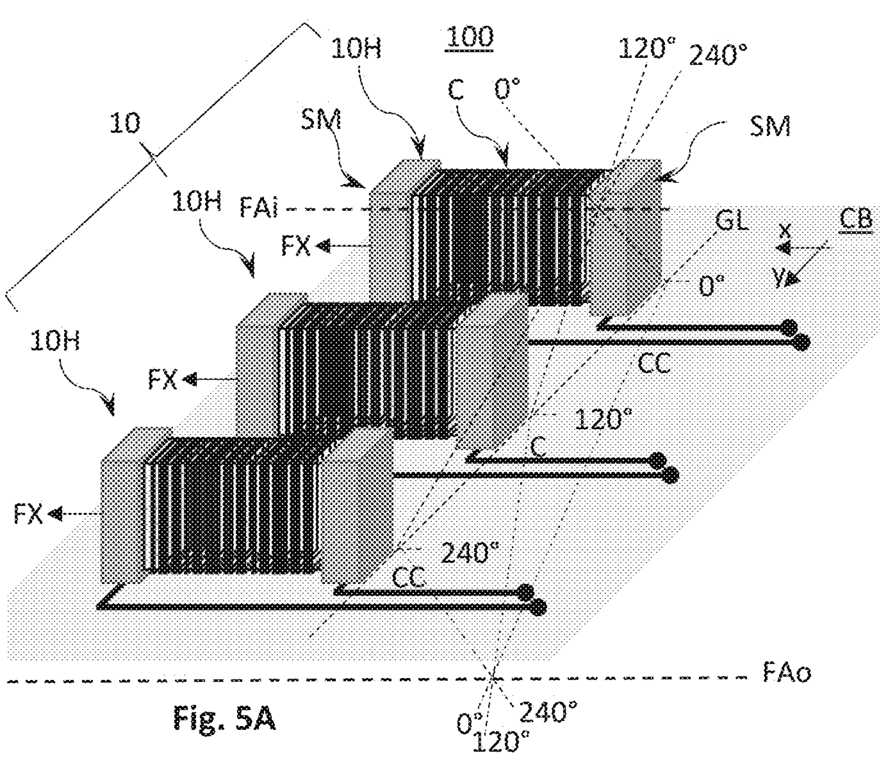
Fig. 5A
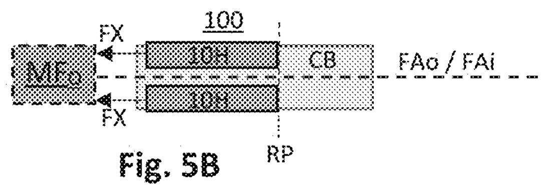
Fig. 5B
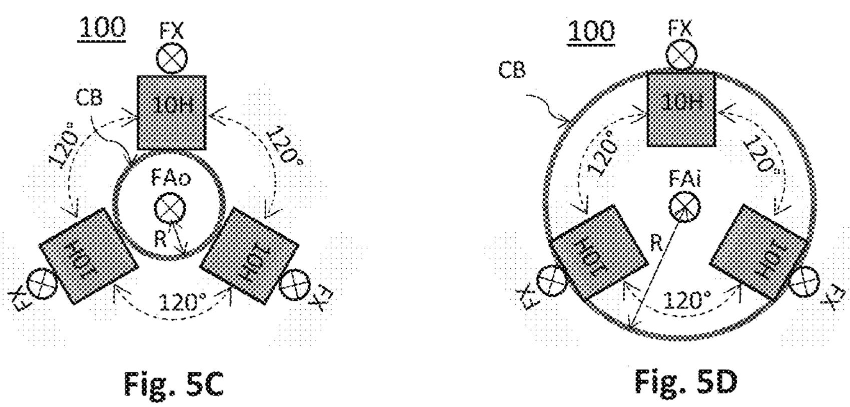
Fig. 5C
Fig. 5D

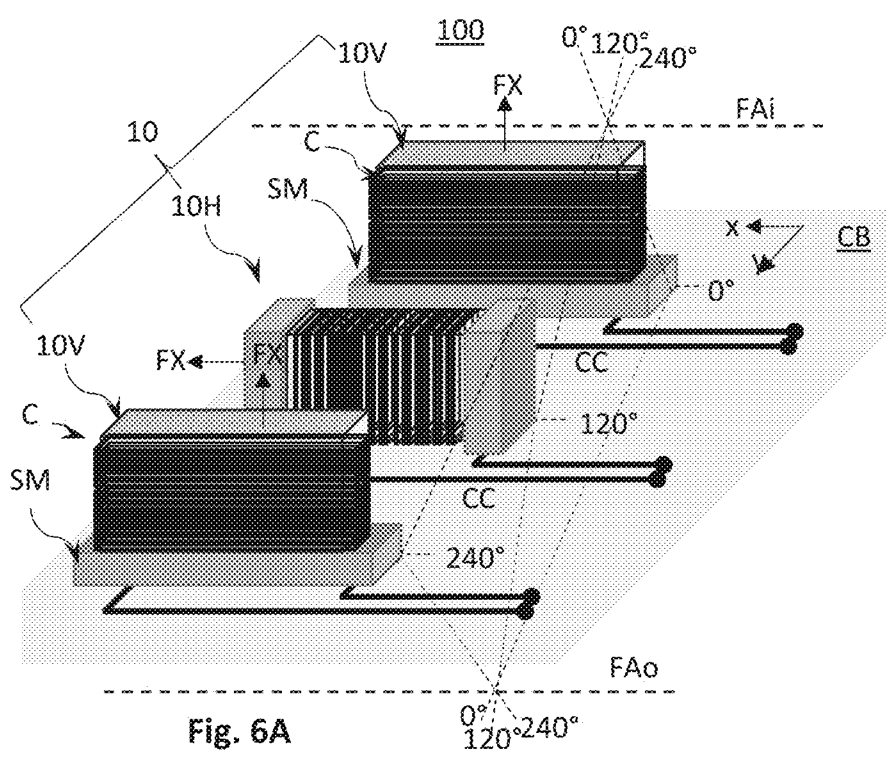
Fig. 6A
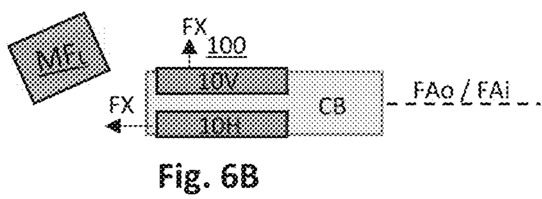
Fig. 6B
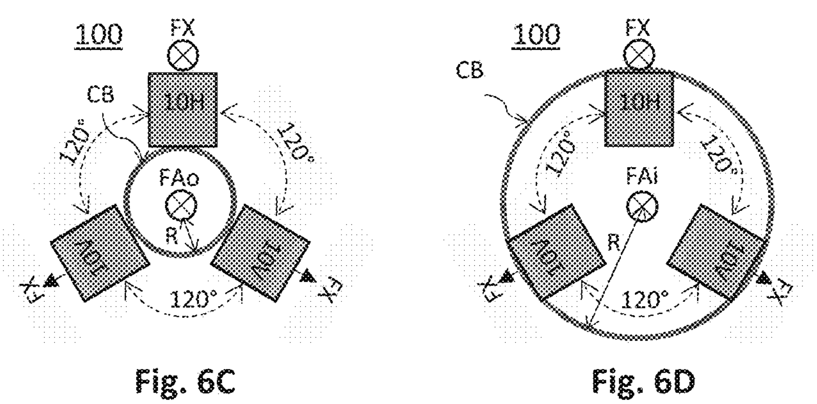
Fig. 6C
Fig. 6D

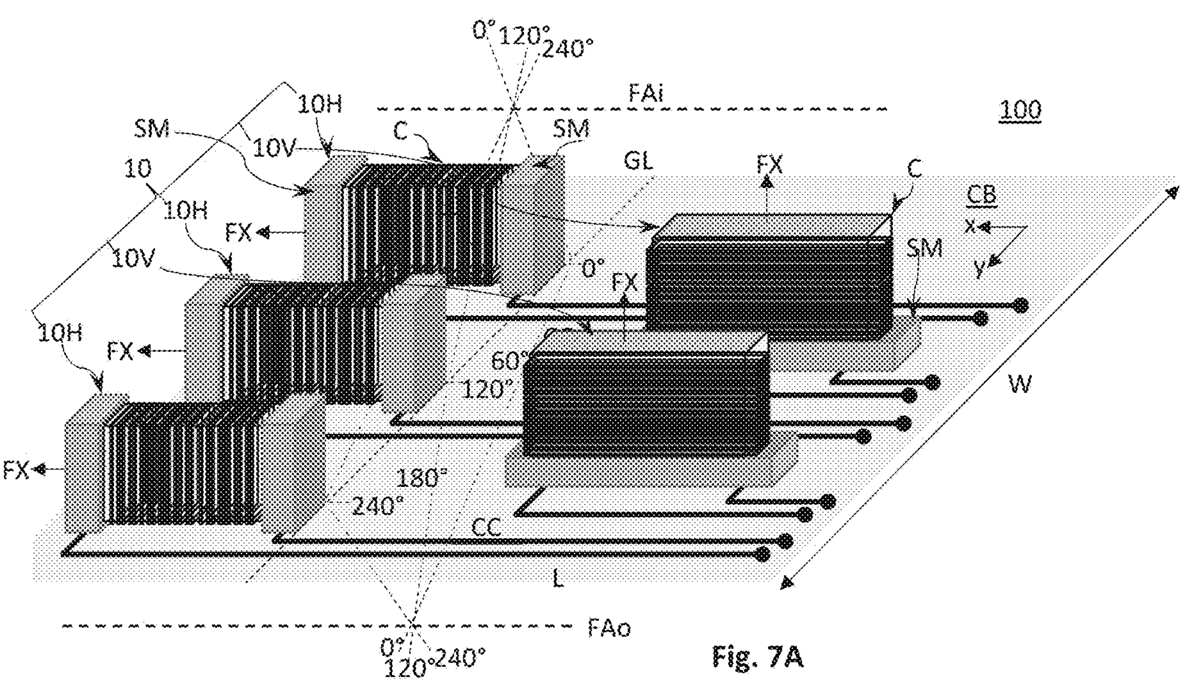
Fig. 7A
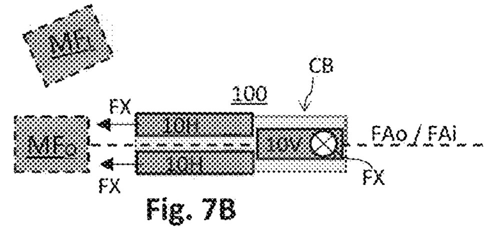
Fig. 7B
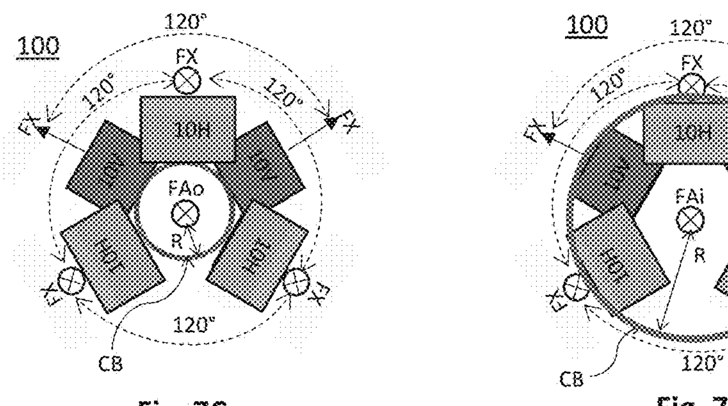
Fig. 7C
Fig. 7D

SYSTEM AND METHOD OF SENSING CATHETERS LOCATION AND FORCE

TECHNOLOGICAL FIELD

The present invention is in the field of catheters and particularly relates to systems and methods for sensing catheter's location and the force applied thereby.

BACKGROUND

In various therapeutic and diagnostic procedures, a catheter/probe is inserted into a patient's body (e.g., chamber of the heart) and to be brought into contact with a body tissue there. Typically, in such procedures, it is necessary to determine the catheter's location within the body (i.e., the location at which a distal tip of the catheter engages the body tissue) as well as the pressure applied thereby to the tissue.

Catheters having integrated location and pressure sensors for sensing the location of the catheter and the pressure/force applied thereby at the contact region with the tissue, are generally known. Such catheters typically utilize inductive coils for determining the location of the catheter within the body and/or the pressure/force applied thereby to a body tissue it engages with.

Conventional techniques for such catheters often utilize wire-winded coils to which a ferrite core may be manually inserted after the winding. The coils fabricated in this way are then soldered to a cable that carries the coil signal to processing circuits, and fitted within the catheter's body.

GENERAL DESCRIPTION

There is a need in the art of catheters, for physically agile and sensitive catheters having compact/narrow dimensions, that are capable of providing accurate feedback on the location of the catheter in the body, and the contact interface between the catheter and the tissue and the force (e.g., vector) applied between them.

U.S. Pat. No. 8,535,308 and U.S. patent application No. U.S. 2020/015693, which are both assigned to the assignee of the present application, disclose for example configurations of such catheters utilizing sensory circuits having several coils, for sensing the location and orientation of the catheter body, as well as the force applied thereby at the interface with the tissue.

One challenge in the art of such catheters is to fit accurate location and force sensors within the narrow body of the catheter, whose lateral dimensions are typically only several millimeters. Indeed, the fabrication of relatively compact coils with sensitivity and dimensions suitable for such catheters and as well as the fitting and electrical connection of these coils within the catheters body typically involve delicate manual operations which are time consuming, costly and may be limited by the achievable compactness and accuracy.

Therefore, there is a need in the art for more efficient, cost-effective techniques for fabrication of such catheters and for the fabrication of small high sensitivity coils (i.e., having high induced voltage in response to magnetic fields; i.e., high impedance) suitable for use for location and or force sensing in catheters such as those disclosed above. Moreover, there is a need in the art for automated fabrication techniques of such coils, yielding standardized coils with less variability between fabricated coils of the same design. Further, in the interest of further advent in the art of catheters, there is also a need in the art to facilitate even smaller and/or of higher impedance/induced-voltage, so as to improve either or both of the sensitivity and agility, and/or reduced dimensions, of the catheter.

The present invention achieves that by providing a novel position sensor, which is particularly suited for furnishing sensor coils of high impedance (high induced-voltage) within the narrow dimensions of a catheter body.

Thus, according to one broad aspect of the present invention, there is provided a position sensor adapted to measure signals indicative of at least one of a location and orientation of the sensor relative to one or more magnetic fields. The position sensor includes a circuit board, and at least three coils located on the circuit board and arranged for sensing different aspects of the magnetic field, which are indicative of at least one of a location and orientation of the sensor relative to the external magnetic field. According some aspects of the invention the circuit board is a flexible circuit board (FCB) and the at least three coils are at least three surface mount coil devices (SMD coils) mounted on the FCB via surface mount technology (SMT). The FCB is furnished at the sensor in folded/rolled state such that the magnetic flux axes of at least three of the SMD coils mounted on its surface are not co-planar to thereby enable to utilize signals obtained from the at least three SMD coils for measuring at least one of the orientation and location of the sensor relative to one or more magnetic field sources.

According to some embodiments the positioning sensor is adapted to measure signals indicative of an orientation of the sensor relative to a first magnetic field source located in-front of the position sensor (e.g. in-front with respect to a longitudinal axis thereof being an axis about which the FCB is folded). The at least three SMD coils include three SMD coils arranged on the FCB such that their magnetic flux axes are parallel to one another and are not co-planar when the FCB is furnished at the sensor in the folded/rolled state. This thereby enable to utilize signals obtained from the three SMD coils to determine two angles of orientation of the relative the first magnetic field source being located in-front of the three SMD coils along a general direction of their magnetic flux axes.

In some embodiments of the invention the three SMD coils are surface mounted to the surface of the FCB via surface mount technology such that their magnetic flux axes are oriented parallel relative to the surface of the FCB at which they are mounted. In turn the FCB is arranged in folded/rolled form at the sensor such that a folding/rolling axis of folded/rolled form of the FCB is substantially parallel to the parallel magnetic flux axes of the three SMD coils thereon.

In some embodiments of the invention the position sensor is adapted to measure signals indicative of location and orientation of the sensor relative to one or more second magnetic field sources. The at least three SMD coils include three SMD coils arranged on the FCB such that when the FCB is folded at the sensor, the magnetic flux axes of the three SMD coils span three dimensional (3D) coordinates. This thereby enables to utilize signals obtained from the three SMD coils to determine a location and an orientation of the sensor relative the one or more magnetic field sources. In some embodiments two SMD coils of the at least three SMD coils of the position sensor are surface mounted to the surface of the FCB via surface mount technology and located on the FCB with vertical orientation of their magnetic flux axes relative to the FCB surface. Accordingly, when the FCB is furnished at the sensor in folded/rolled state, the magnetic flux axes of the two SMD coils are not parallel. A third SMD coil of the at least three SMD coils is surface mounted to the surface of the FCB via surface mount technology with parallel orientation of its magnetic flux axis relative to the FCB surface. This thereby enables to utilize signals obtained from the three SMD coils in order to determine a location and orientation of the sensor relative to the one or more external magnetic field sources.

According to some embodiments of the present invention the position sensor includes at least five SMD coils surface mounted to one or more FCBs of the sensor. A first subset of three SMD coils of the at least five SMD coils are arranged such that their magnetic flux axes are parallel to one another and are not co-planar when the FCB is furnished at the sensor in folded/rolled state to thereby enable utilization of the signals obtained thereby to determine two angles of orientation of the sensor relative to the first magnetic field source located in-front of these three SMD coils along a general direction of their magnetic flux axes. Additionally, a second subset of three SMD coils of the at least five SMD coils are arranged such that when the FCB is furnished at the sensor in folded/rolled state, the magnetic flux axes thereof span 3D coordinates. This thereby enables utilization of the signals obtained from the three SMD coils of the second subset to determine a location and orientation of the sensor relative one or more second magnetic field sources.

According to some embodiments at least one SMD coil of the at least three SMD coils of the sensor includes a coil portion and at least one surface mount portion arranged from at least one respective side of the coil portion. The coil portion includes a ferrite core and a conductive winding arrangement arranged in a helix directly over an external surface of the ferrite core with a pitch of the helix not exceeding 13 μm and in some embodiments not exceeding 12 μm to thereby provide that the SMD-Coil has compact dimensions and high impedance. In some implementations the ferrite core may for instance include material of relative magnetic permeability u, in the order of at least 100 which is stable with tolerance of ±0.3% within a temperature range between about 20° C. to 60° C. This thereby enables consistent magnetic field measurements during operation under variable temperature conditions within said temperature range. In some implementations the conductive winding arrangement are fabricated directly over the external surface of the ferrite core, utilizing photolithography.

In some embodiments of the position sensor of the invention, at least one SMD coil of the at least three SMD coils is mounted on the FCB with a flat/parallel orientation of its magnetic flux axis relative to the FCB surface. The at least one SMD coil includes a coil portion having a conductive winding arrangement, and at least two SMT-mounting portions arranged from opposite sides of the coil portion and having at least two respective electric contacts electrically coupled to the FCB with SMT electrical connection, and respectively electrically connected to opposite ends of the conductive winding arrangement.

In some embodiments of the position sensor of the invention, at least one SMD coil of the at least three SMD coils is mounted in a vertical/perpendicular orientation of its magnetic flux axis relative to the FCB surface. The at least one SMD coil includes a coil portion having a conductive winding arrangement and at least one SMT-mounting portion arranged from at least one side of the coil portion and having at least two electric contacts electrically coupled to the FCB via SMT electrical connection and respectively electrically connected to opposite ends of the conductive winding arrangement. According to further broad aspect of the present invention there is provided a medical instrument/device including a position sensor configured and operable according to the present invention as described above a further described in more details below. According to some embodiments the medical instrument is a catheter having an elongated housing including a main section having a longitudinal axis, and a tip section flexibly coupled at a distal end of the main section and including the first magnetic field source. The position sensor is accommodated at the main section of the elongated housing such that said FCB being folded/rolled about an axis parallel to the longitudinal axis of the catheter. The first subset of coils of the sensor, as described above, facilitates determining an orientation of the tip section relative to the main section of the housing based on measurement of magnetic fields from the first magnetic field source that is located at the tip section. The second subset of coils of the sensor, as described above, facilitates determining a location and an orientation of the main section relative to the one or more external second magnetic field sources (which may be located externally to the medical instrument).

According to yet another broad aspect of the present invention there is provided a method to fabricate a magnetic position sensor suitable for use in a medical instrument. The method includes:

i. providing a flexible circuit board (FCB);
ii. providing at least three surface mount coil devices (SMD coils);
iii. mounting the at least three SMD coils to the FCB via surface mount technology (SMT);
iv. folding the FCB, with the at least three SMD coils thereon, into tubular form, such that magnetic axes of the at least three SMD coils are not coplanar and may thereby providing that magnetic fields sensed thereby from one or more magnetic field sources, enable measurement of at least one of a location and orientation of the sensor relative to the sources.

In some embodiments, e.g. where the medical instrument is a catheter having a body of tubular shape with characteristic inner diameter of about 2.5 millimeters or less. The folding is carried out such that a diameter of the FCB after being folded is smaller than the characteristic inner diameter of the body of the catheter; and the method includes placing the folded FCB within said body.

According to some embodiments the magnetic position sensor is adapted to measure signals indicative of an orientation of the sensor relative to a magnetic field source. The mounting of the at least three SMD coils includes mounting three of the SMD coils on the FCB such that their magnetic flux axes are parallel to one another and are not co-planar when the FCB is folded to the tubular form, to thereby enable to utilizing signals obtained from these three SMD coils to determine two angles of orientation of the relative a magnetic field source located in-front of the three SMD coils along a general direction of their magnetic flux axes.

According to some embodiments the magnetic position sensor is adapted to measure signals indicative of location and orientation of the sensor relative to one or more external magnetic field sources. The mounting of the at least three SMD coils includes mounting three of the SMD coils on the FCB such that when the FCB is folded to the tubular form, the magnetic flux axes of these three SMD coils span 3D coordinates, to thereby enable utilizing signals obtained from the three SMD coils to determine location and orientation of the sensor relative the external magnetic field sources.

According to some embodiments, the magnetic position sensor is adapted to measure signals indicative of an orientation of the sensor relative a first magnetic field source and signals indicative of location and orientation of the sensor relative to one or more second external magnetic field sources. The at least three SMD coils include at least five SMD, and the mounting includes mounting the at least five SMD coils such that the following arrangement of magnetic flux axes thereof is obtained when the FCB is folded into to the tubular form:

the magnetic flux axes of a first subset, which includes at least three SMD coils of the at least five SMD coils, are parallel to one another and are not co-planar to thereby facilitate utilization of signals obtained from said first subset to determine two angles of orientation relative to the first magnetic field source when being located in-front of the three SMD coils of the first subset along a general direction of their parallel magnetic flux axes;

the magnetic flux axes of a second subset, which includes at least three SMD coils of the at least five SMD coils, span 3D coordinates to thereby facilitate utilization of signals obtained from said first subset to determine location and orientation of the sensor relative the one or more external magnetic field sources.

In some embodiments the mounting is performed utilizing surface mount technology and includes at least one of the following:

mounting at least two SMD coils with vertical orientation of their magnetic flux axes relative to the FCB surface; and mounting at least one SMD coil with parallel orientation of its magnetic flux axis relative to the FCB surface; such that when the FCB is in folded state, the magnetic flux axes of the at least two SMD coils and the at least one SMD coil span 3D coordinates; and mounting at least three SMD coils with parallel orientation of their magnetic flux axes relative to the FCB surface such that when the FCB is folded about an axis parallel to of the magnetic flux axes, the magnetic flux axes of said three SMD coils are parallel and not co-planar;

In some implementations the providing of the at least three SMD coils includes fabricating at least one SMD coil of the SMD coils utilizing a photolithographic method of the present invention and thereby forming helical windings directly on a ferrite core of the coil. The photolithographic method includes for example:

a. applying photoresist layer to cover at least a tubular section of the ferrite core;
b. applying photolithography to pattern a photoresist layer to form a helical pattern over the tubular section covered by the photoresist layer; and
c. electroplating an external surface layer of the ferrite core, at the exposed regions of the helical pattern, to form the conductive helical windings directly on an external surface layer of the tubular section of the ferrite core.

In some embodiments the photolithographic fabrication method is further characterized by one or more of the following:

the photolithographic method is adapted for fabrication of high-density conductive windings, and a pitch of the helical pattern formed by the photolithography (and correspondingly of the pitch of the conductive helical windings) is in the order of, or less than, 10 μm;

the ferrite core includes fully sintered magnetic material having relative magnetic permeability u, in the order of at least 100; and wherein the photolithography is performed utilizing a photolithographic light source with light power density (LDP) and wavelength suited for patterning the photoresists while not inducing substantial damage to the ferrite core;

The application of the photoresist layer includes applying a layer of dry photoresist with thickness of at least 8 μm to thereby enable the electroplating of the external surface layer while yielding narrow line width of the helical conductive windings with small pitch between adjacent lines and preventing spread of the electroplating between them;

The photolithographic fabrication method includes fabricating a seed layer prior to the electroplating, whereby the seed layer is fabricated over at least a section of the ferrite core in order to increase a surface conductivity of the ferrite and facilitate the electroplating;

The photolithographic fabrication method includes, after the electroplating, removing remaining photoresists material between conductive windings of the helical coil;

The ferrite core is provided with at least one surface mount portion arranged from at least one respective side thereof; and the photoresist, photolithography and electroplating are applied to also form one or more conductive couplings between at least one end of the conductive helical coil and one or more designated locations on the at least one surface mount portion, to thereby form one or more SMT contacts.

To this end, the inventors of the present invention have also conceived novel and inventive configurations of surface mounted coils devices (SMD-Coils) as well as methods of fabrication of such SMD-Coils, to facilitate the properties of high impedance and small dimensions of the SMD-Coils as desired in general for many sensor applications, and in particular for catheter sensory systems. In this regard, desired traits for such SMD-Coils include inter-alia high density helical windings closely packed over a tubular high permeability and electrically insulating magnetic core, and more specifically high-count helical windings/turns per unit length of the tubular magnetic core and per winding layer thereover. For example, achievable by lithography-based coil fabrication methods of the present invention is a high-density winding with winding count in the order of at least 100 to 150 turns per millimeter of core length (e.g., per winding layer) directly over a magnetic core. Additionally, wire-winding coil fabrication techniques of the present invention facilitate high-density winding with multiple winding layers and with winding count in the order of about 80 turns per layer per millimeter of core length (e.g., 77-83 turns per layer per millimeter), directly over the core. Moreover, the coil fabrication techniques of the invention facilitate the fabrication of the windings over high-permeability (and electrically insulating) tubular magnetic core with relative permeability in the order of hundreds or more (e.g., relative permeability $\mu_r$ of at least 100). It is noted that the term relative permeability $\mu_r$ is used herein to designate a dimensionless number representing the ratio between the permeability of a magnetic material μ relative to the permeability of space $\mu_0$; i.e. $\mu_r=\mu/\mu_0$.

In this regard it should be understood that the term tubular is used herein to generally designate a body having a longitudinal axis of symmetry for discrete set or continuous set of rotations (i.e., generally any shape, such as cylindrical or conic shape having a longitudinal axis of symmetry, e.g., along its z axis, and lateral cross-section in the x-y plane, which may be smooth, e.g., circular or elliptic, or polygonal, e.g., triangle, rectangle etc.).

In this connection, aspects of the present invention particularly pertain to Helical SMD-coils having tubular magnetic cores, with one or more helical conductive windings arranged over the tubular magnetic core (in case of a plurality of helical conductive windings, the plurality of helical windings may be connected in series or parallel and may be arranged concentrically about the core). The helical conductive windings may have elliptic, circular, polygonal cross-sectional shape, which typically follows the core's cross-section. In this connection, it should also be note that the helical configuration of the Helical SMD-coils of the present invention is considered advantageous over other types of coils such as planar coils (e.g., planar concentric coils) or "air core" coils (i.e., having no magnetic material core). The advantages are particularly eminent in cases where highly inductive coils (e.g., coils of higher reactance/induced-voltage at designated frequencies) of compact cross-section are concerned, as in the case of compact sensory systems such as those used in catheters. This is because as per similar voltage induced by external magnetic fields (e.g., time varying magnetic fields external to the coil), the helical SMD-coils of the invention may be fabricated with smaller size and/or smaller cross-section as compared to planar coils as planar concentric coils (in which magnetic core, if exists, lays below the planar coil). More over the helical SMD-coils of various embodiments of the invention are designed for Surface Mount assembly on electronic circuitry, thus enabling more efficient, fast reliable and cost-effective assembly of the coils on sensor circuits. Yet additionally, in the fabrication technique of the invention, the compact helical SMD-coils are fabricated with the windings formed/wrapped over the magnetic core (differently from some conventional techniques of compact high winding count coil fabrication which require an additional post-winding (manual) step of inserting the core within the windings). This also in turn facilitates a more cost-effective fabrication process of compact coils with uniform production yield.

It should be noted that the term magnetic core, as well as the terms ferrite and ferrite core, which are used herein interchangeably, are used herein to designate a bulk/body of magnetic material/composition or mixture, with relative permeability $\mu_r$>>1. The terms substantially pure magnetic material and pure ferrite are used herein to designate a bulk/body of material which has relative permeability $\mu_r$>>1 and which is substantially not mixed/compound with other materials. This is particularly to distinguish such magnetic-materials, from compounds/mixtures of magnetic-materials with non-magnetic-materials, such as epoxy, which are often used to improve properties of the ferrite cores other than its permeability $\mu$, such as core formation at low temperature while at the expense of compromising the resulting permeability of a core made with such compounds/mixtures.

In this regard, as would be appreciated by those versed in the art, magnetic material suited for the SMD-Coils of the present invention are typically of a type having magnetic properties of a so called soft-ferrite (i.e., having relatively low coercivity making it suitable for use in electrical applications such as inductors).

Cores of substantially pure magnetic materials, are typically sintered to form a solid structure, yet the sintered structure remains relatively physically weak/brittle and easily damageable during fabrication processes. For instance, a bulk of pure soft magnetic material/core may be susceptible to structurally damage (fractured/breakage) under the pressure applied thereto during physical wire winding process. In another example the surface composition and crystalline structure of ferrite core (e.g. of substantially pure/un-mixed magnetic material) may be relatively easily damaged when exposed to high intensity light, for example when using a laser to ablate copper from the ferrite surface, which may generate surface temperature greater than 1000 C, leading to conversion of the material conductivity properties e.g. turning it from electrically insulating material to relatively conducting material, which may be less desired for electrical applications such as instance/transformer/filter coils etc., Therefore, many conventional techniques for coil fabrication, and particularly for fabrication of tubular coils, favor the use of mixed/compound of magnetic material(s) with other materials (e.g., structurally enforcing materials) so as to improve the physical strength of the core compounded in this way and/or stabilize its electric resistivity against manufacturing processes and/or other environmental conditions, on expense of lowering its total permeability. To this end, standard technique for fabrication of chip scale inductors (of few millimeter in size) with fully sintered ferrite cores, are limited with respect to the maximal allowed aspect ratio between the core length and its lateral dimension (the core cannot be too long since the core will break during the winding) and also limited in the minimal allowed diameter of the winded wire, which is typically not be less that 20-25 μm (since thinner wires will break due to tension applied thereto during a conventional winding process).

Thus, in accordance with the above, the conventional techniques for fabrication of helical surface-mountable coils, are limited and less suited for fabrication of compact helical SMD-coils having high density of windings over a magnetic-core of highly permeable (e.g., substantially pure) magnetic materials (particularly over a "soft" magnetic-core), and are also associated with high costs for fabrication of such coils and with non-uniform production yield.

Advantageously, the present invention provides novel and inventive Helical SMD coil fabrication techniques and novel and inventive Helical SMD coil configurations facilitating to overcome some or all of the above deficiencies of the conventional techniques, that enable substantially automated fabrication of compact Helical SMD coils having high winding density (with wire-winding pitch down to a few microns) over highly permeable magnetic materials while alleviating some of the geometrical restrictions imposed by the conventional techniques on fabrication of such coils (such as limitation on the permissible aspect ratio), while advantageously yielding a more uniform production yield.

Thus, according to one broad aspect of the invention there is provided a surface mounted coil device (SMD-Coil). The SMD-Coil includes a coil portion having a ferrite core; and conductive winding arrangement which includes a conductor arranged in a helix that circumferences the ferrite core about a longitudinal axis thereof. The SMD-Coil also includes at least one surface mount portion, arranged from at least one respective side of the coil portion, and having at least one electric contact coupler for electrically coupling the conductive winding arrangement of the coil portion to a circuit via surface mount technology (SMT). According to some embodiments of the invention the continuous conductor of the conductive winding arrangement, is winded directly over an external surface layer of the ferrite core whereby a pitch of conductive windings in the helical conductive winding arrangement does not exceed 12 or 13 μm. Accordingly, the SMD-Coil is obtained with compact dimensions and high impedance (yielding high magnetic field induced voltage) which is particularly suitable for SMT installment in magnetic field sensors.

According to some embodiments of the present invention the SMD-Coil is configured for flat/parallel installation on a surface of a circuit. In such embodiments at least two SMT-mounting portions are arranged from opposite sides of the coil portion and each of them includes at least one electric contact electrically connected to the conductive winding arrangement from a respective end thereof. The SMT-mounting portions with said electric contacts are therefore suitable for SMT installation on a circuit board such that the SMD-coil is mountable to the circuit board surface with its magnetic flux axis substantially parallel to the surface of the circuit board.

Alternatively, or additionally, according to some embodiments of the present invention the SMD-coil is configured for vertical/perpendicular installation on the surface of a circuit board. In such embodiments the at least one SMT-mounting portion may be a single SMT-mounting portion including at least two electric contacts respectively electrically connected near about opposite ends of the conductive winding arrangement and suitable for the SMT installation on the circuit board. The SMD-coil is thereby mountable to the surface of a circuit board surface with its magnetic flux axis substantially perpendicular to the circuit's surface.

According to some embodiments of the present invention the ferrite core of the SMD-Coil includes material of relative magnetic permeability $\mu_r$ in the order of at least 100 and the relative magnetic permeability of the ferrite core material is stable (with tolerance of ±0.3%) within a temperature range between about 20° C. to 60° C. This thereby enables consistent magnetic field measurements during operation under variable temperature conditions within said temperature range.

According to yet another broad aspect of the present invention there is provided a method for fabricating a helical coil directly on a ferrite core such that its circumferences the ferrite core. The method includes:

a. providing a ferrite core having a tubular shape;
b. applying photoresist layer to a circumference part of the surface of the ferrite core to cover at least a tubular section thereof from all side;
c. applying photolithography to pattern the photoresist layer to form a helical pattern over the tubular section of the ferrite core covered by the photoresist layer; and
d. electroplating an external surface layer of the ferrite core at the exposed regions of the helical pattern to form the conductive helical coil over the external surface layer of the ferrite core with a form of said helical pattern.

According to some embodiments of the invention the method is adapted for fabrication of the conductive helical coil with high density windings, whereby a pitch of the helical pattern and correspondingly of the conductive helical coil is in the order of, or less than 10 μm (and even down to 8 μm).

According to some embodiments of the method, the ferrite core includes, or is constituted by, fully sintered magnetic material having relative magnetic permeability $\mu_r$ in the order of at least 100. To this end the above indicated photolithography operation may utilizes a photolithographic light source providing light power density (LPD) and wavelength suited for patterning the photoresists while not inducing substantial damage to the ferrite core.

In some implementation of the method, the application of the photoresist layer includes applying a layer of dry photoresist with thickness of at least 8 μm. This thereby enables the electroplating operation to yield narrow line width of the helical conductive coil with small pitch between adjacent lines while preventing spread of the electroplating between the lines.

In some implementation the method further includes fabrication of a seed layer over at least a section of the ferrite core in order to increase a surface conductivity of the ferrite to facilitate the electroplating. Additionally, or alternatively, in some implementation of the method, after the electroplating, remaining photoresists material is removed from between conductive windings of the helical coil.

According to some embodiments of the present invention the method is adapted to fabricate further elements of the surface mounted coil device (SMD-Coil). The method may further include one or more of the following:

- in operation a. the ferrite core is provided with at least one surface mount portion arranged from at least one respective side thereof;
- in operation b. the photoresist layer is applied also to a surface region of the at least one surface mount portion, which extends from the ferrite core towards a designated electric contact location on the surface mount portion;
- in operation c. the photolithography is applied to pattern the photoresist layer at the surface region of at least one surface mount portion to form a patterned path connecting one end of the helical pattern to the designated location at the surface mount portion; and
- in operation d. the electroplating is applied to the patterned path to form a conductive coupling between the end of the conductive helical coil and the designated location at the surface mount portion.

According to some embodiments of the present invention the method is adapted for fabrication of a surface mounted coil device (SMD-Coil) suitable for flat/parallel installment on a circuit surface. In such embodiments the ferrite core may be provided with at least two surface mount portions, arranged from at least two respective side thereof. Accordingly, operations (b.) to (d.) may be applied to form respective conductive couplings between two designated locations at the respective surface mount portions and corresponding ends of said conductive helical coil. This thereby enables flat/parallel installment of the SMD-Coil on a surface of a circuit board, with the two designated locations at the two surface mount portions respectively providing electric contacts between circuit and respective ends of the conductive helical coil.

Alternatively, or additionally, according to some embodiments of the present invention the method is adapted for fabrication of a surface mounted coil device (SMD-Coil) which is adapted vertical/perpendicular installment on a surface of a circuit board. The ferrite core may be provided in this case with at least one/single surface mount portion arranged from one side thereof. The ferrite core may in this case also include a conductive bulk path that passes through a bulk of the ferrite core from an electric contact of the surface mount portion located at said one respective side, towards an opposite side of the ferrite core at which a conductive region of the conductive path is exposed. Accordingly in such embodiments the operations (b.) to (d.) of the method may be applied to form:

(i) conductive couplings between a designated locations at said surface mount portion and a corresponding end of said conductive helical coil which is located proximal to said surface mount portion; and
(ii) conductive couplings between said exposed conductive region of the conductive bulk path and a corresponding end of said conductive helical coil which is located proximal to said exposed conductive region;

The method according to such embodiments enables vertical/perpendicular installment of the SMD-Coil on a circuit, with the electric contact at the single surface mount portion providing electric contacts between the circuit and respective ends of the conductive helical coil.

According to yet another broad aspect of the invention there is provided a method for fabricating a surface mounted coil device having a helical coil directly on a ferrite core and to circumference the ferrite core. The method according to this aspect includes:

a. Providing a ferrite core having a tubular shape; and
b. Windings conductive wire over the ferrite core to form a helical coil over a circumference of the ferrite core;
c. Attaching one or more surface mount portions to one or more respective sides of the ferrite core and electrically connecting two ends of the helical coil to two respective electric contacts of the one or more surface mount portions.

According to the invention the conductive wire used in the windings has a characteristic diameter in the order of about 12 to 13 micrometers or less. This thereby facilitates high density windings over the ferrite core and correspondingly improved coupling of the coil to magnetic fields (high induced voltage).

According to some embodiments the ferrite core is comprises fully sintered magnetic material (i.e., with no non-magnetic structurally enforcing additives) thereby providing relative magnetic permeability $\mu_r$ in the order of at least 100 or higher.

In yet additional broad aspect of the present invention there is provided a surface mounted coil device (SMD-Coil) including a coil portion having a ferrite core and a conductive winding arrangement. The conductive winding arrangement includes a conductor arranged in a helix that circumferences the ferrite core about a longitudinal axis thereof. The SMD-Coil also includes at least one surface mount portion, arranged from at least one respective side of the coil portion, and having at least one electric contact coupler for electrically coupling the conductive winding arrangement of the coil portion to a circuit via surface mount technology (SMT). The SMD-Coil is fabricated according to any one of the methods of the present invention described above such that the continuous conductor of the conductive winding arrangement is winded/arranged directly over an external surface layer of the ferrite core with a pitch of the helix of the conductive winding arrangement not exceeding 13 μm and in some cases not exceeding 12 μm.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 5A, 5B, 5C and to 5D, 6A, 6B, 6C and to 6D, 7A, 7B, 7C and 7D and 8A, 8B, 8C and to 8D are schematic illustrations of a position sensor 100 according to several embodiments of the present invention;

FIG. 10A is a flow diagram of the method, and FIG. 10B illustrates the folding of the circuit board of the sensor during the fabrication.

DETAILED DESCRIPTION OF EMBODIMENTS

Figure 1A:
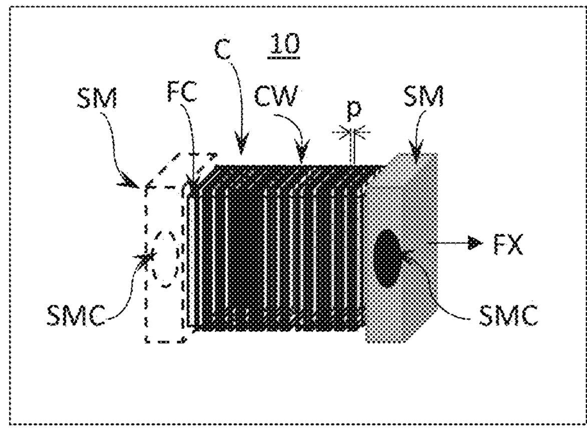
FIGS. 1A, 1B and 1C are schematic perspective views of helical surface mounted coil devices (SMD-Coils), each configured according to an embodiment of the present invention.

Reference is now made to FIG. 1A in which a perspective view of a helical surface mounted coil device (SMD-Coil) 10 according to an embodiment of the present invention is illustrated. The SMD-Coil 10 generally includes a Coil Portion C having a core FC of magnetic material (also referred to herein interchangeable as Ferrite Core) and a conductive winding arrangement CW, which includes a conductor which is arranged in a helix that is winded around the magnetic core FC about a longitudinal axis FX thereof. The SMD-Coil 10 also includes one or more Surface Mount Portions SM (typically comprising non-magnetic materials such as copper and tin, and/or magnetic nickel and tin), arranged from at least one respective longitudinal end of the Coil Portion C, and having thereon at least two electric contact couplers SMC conductively coupled near/at respective ends of the conductor of the conductive winding arrangement CW of the Coil Portion C and adapted for electrically coupling the conductive winding arrangement CW to a circuit via Surface Mount technology (SMT). Preferably in some embodiments the size, location and materials of these contacts are configured as not to shield the external magnetic field going into the magnetic core, and may even to assist in funneling magnetic field to the core.

Specifically in the helical SMD-Coil 10 according to this embodiment of the invention, the continuous conductor of the conductive winding arrangement CW, has a helical geometry and is winded/wrapped directly over an external surface of the magnetic core FC, for example on the on the bare surface of the magnetic material of the magnetic core FC, or on a seed layer which may be fabricated on the magnetic material of the core FC, for example in order facilitate that a conductivity of the core's surface is sufficient for electroplating process by which the conductive winding arrangement CW is fabricated on the core FC according to some embodiments of the present invention, as described below.

Figure 2:
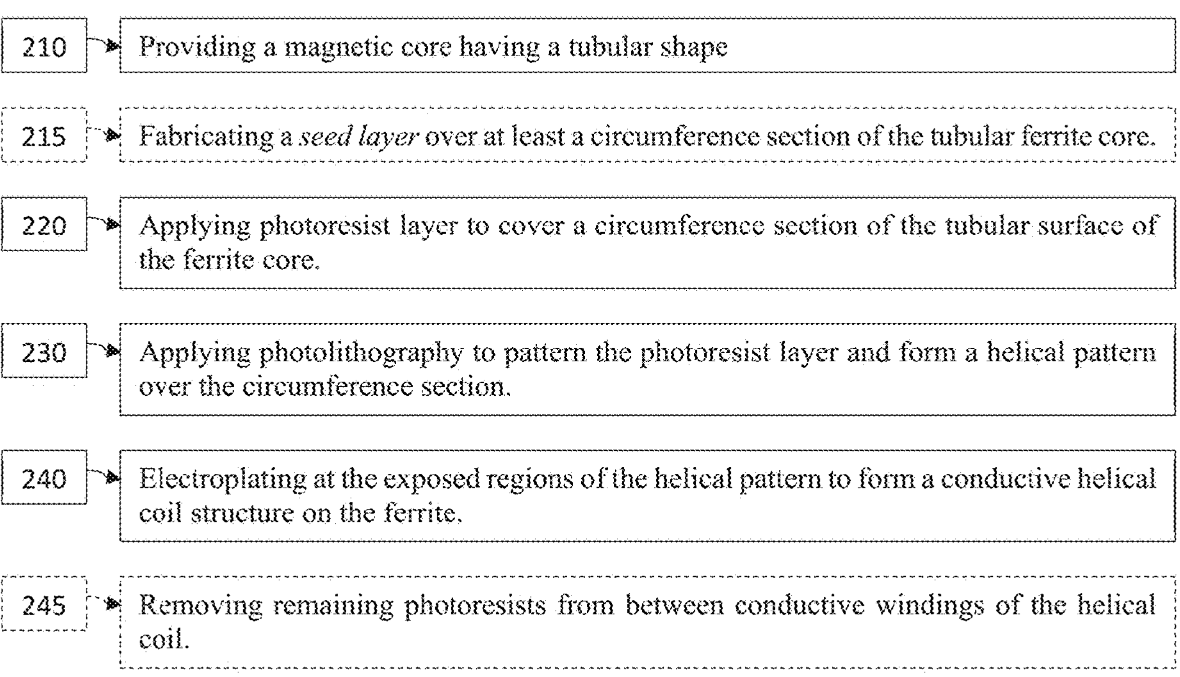
FIG. 2 is a flow diagram of a lithography-based method of fabrication of a helical SMD-Coil according to an embodiment the present invention.
Figure 3:
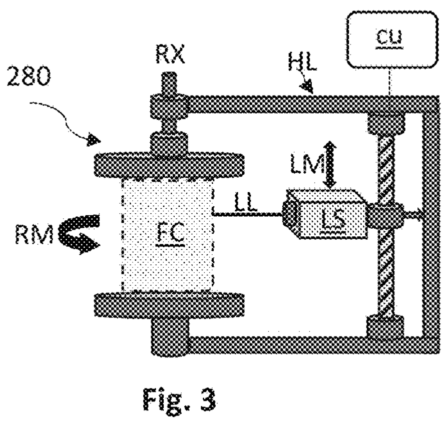
FIG. 3 is a schematic illustration of a in which an example of a photolithographic coil fabrication system according to an embodiment of the present invention.
Figure 4:
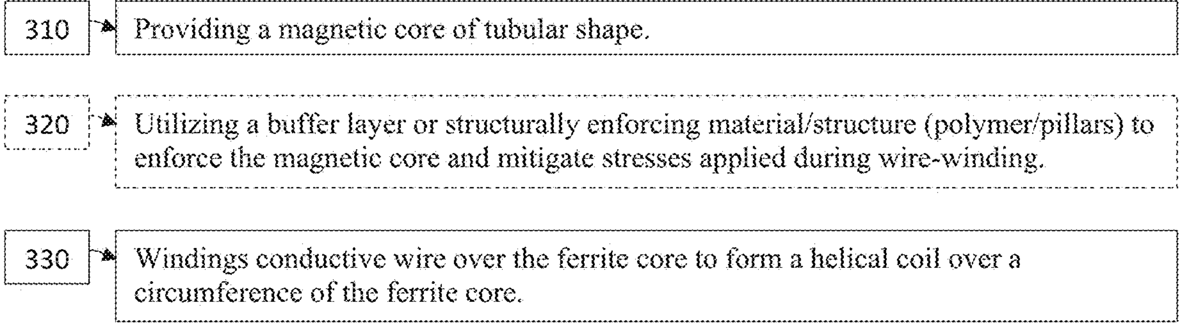
FIG. 4 is a flow diagram of method of fabrication of a compact helical SMD-Coil utilizing wire-winding, according to an embodiment the present invention.
Figures 8A, 8B, 8C, 8D:
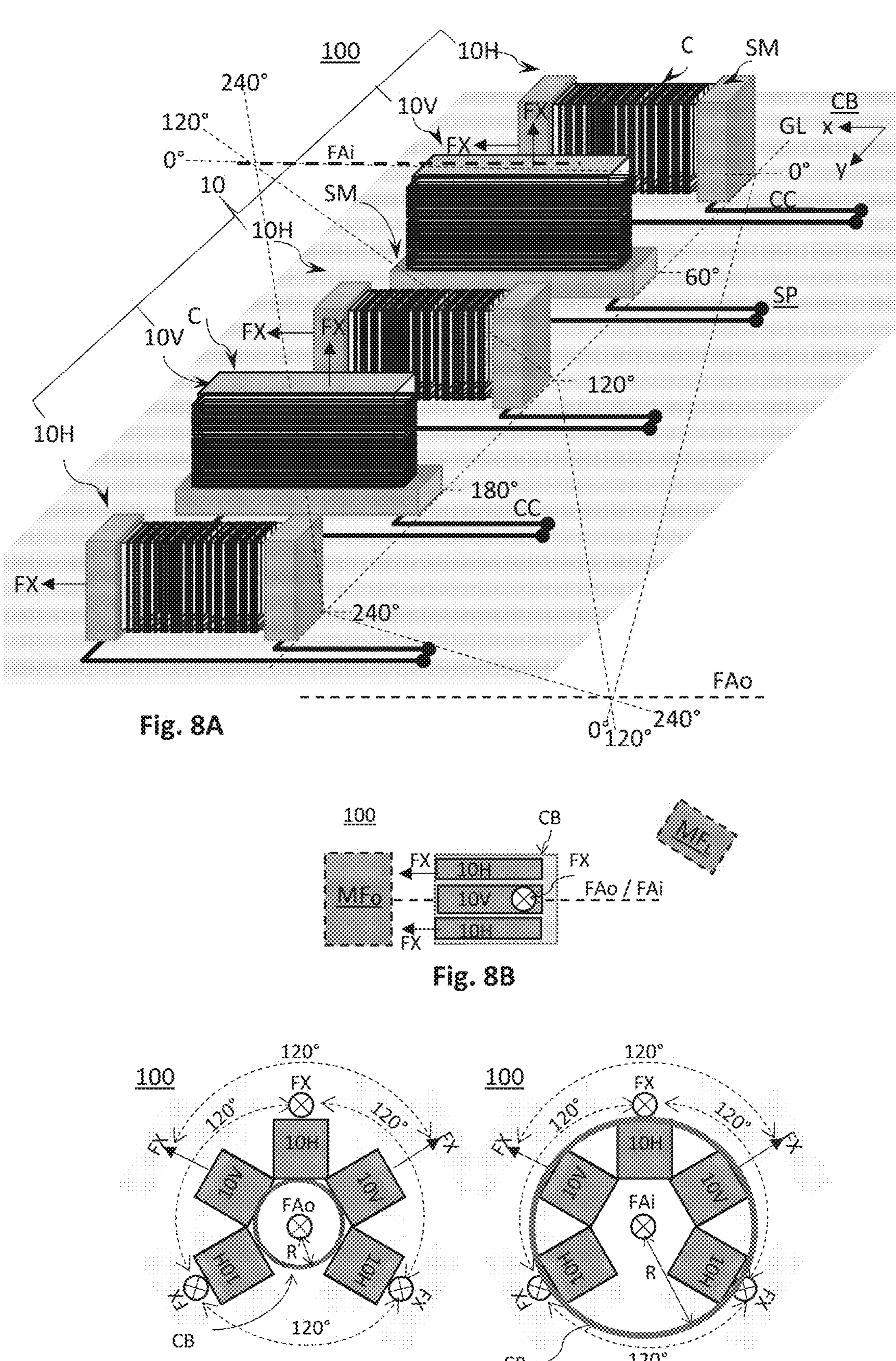

It should be understood that in the context of the present application, the phrases related to winding and/or winded are used to designate the formation of conductive helical structure (the conductive winding arrangement CW) about the magnetic core FC regardless of the specific method used for fabrication of this structure, whether by lithography as exemplified in FIGS. 2 and 3, or by wrapping of conductive wire over the core as exemplified in FIG. 4.

Moreover the helical SMD-Coil 10 according to this embodiment of the invention is specifically configured to yield high inductance and high induced voltage for a designated range of frequencies, and may be predesigned for the designated range of frequencies by proper selection of the magnetic core material according to its permeability at the designated range of frequencies, as well as the cross-sectional area of the core FC and the number of windings in conductive winding arrangement CW by which the induced voltage and inductance of the coil may be defined. In a particular non-limiting example, the helical SMD-Coil 10 may be specifically configured to yield high inductance and reactance for frequencies in the KHz regime, e.g., 1 to 16 KHz which may be particularly suitable for use in magnetic field positioning and force sensors such as those used in catheter applications.

In this regard, in order to facilitate accurate and consistent sensory measurements within a range of operational temperature conditions [$T_{min}$, $T_{max}$], the magnetic material of the core C is preferably selected such that its permeability u is substantially stable within the required operational temperature range [$T_{min}$, $T_{max}$] with variability of the permeability $\mu_r$ not exceeding for example ±0.3% (e.g., not exceeding about 160 ppm/C) within said temperature range [$T_{min}$=20 C, $T_{max}$=60 C]. In this connection it is noted that generally the shorter the magnetic core along its longitudinal axis, its temperature coefficient can be higher without effecting stability.

In a particular non-limiting example, the permeability u of the magnetic material of the core FC is substantially stable (e.g., within said tolerance) within a temperature range between about 20° C. to 60° C. to thereby facilitate accurate operation of a sensor utilizing said helical SMD-Coil 10 when furnished in catheters, such as ablation catheters, whose surgical function may yield variations of the temperatures within said temperatures range.

Furthermore, according to embodiments of the present invention, in order to facilitate high inductance/induced voltage of the helical SMD-Coil 10 of the invention, together with compact dimensions, the magnetic material of the core FC is preferably selected such that its magnetic relative permeability $\mu_r$ is in the order of hundreds (e.g., at least 100) at the designated operational magnetic field frequency range (which may be for example within a range of about 1 to 16 KHz). To this end, preferably in order to obtain such high permeabilities of the core FC in some embodiments the magnetic material used in the core FC includes, or is constituted by, sintered/fully-sintered magnetic material such as ferrite (e.g., without mixture with substantial amounts of non-magnetic materials such as structurally enforcing additives; e.g., epoxy). Preferably the magnetic core FC material used is temperature stable in the temperature range of 20° C. to 60° C. (e.g., with temperature coefficient of permeability of less than <160 ppm/° C.).

Additionally, preferably in order to facilitate the high inductance/induced voltage of the helical-SMD-Coil 10, the conductor helix of the conductive winding arrangement CW is configured with pitch P not exceeding 8-14 μm of the helical windings/turns. For instance, embodiments of the SMD-Coil fabrication techniques of the present invention described below with reference to FIGS. 2 and 3, facilitate fabrication of conductive winding arrangement CW with winding pitch P of about 8 μm (e.g., with conductor's lateral diameter/width down to 4 μm and even smaller and spacing between consecutive turns down to 4 μm and even smaller, thereby yielding pitch P of 8 μm or less). In another instance, embodiments of the SMD-Coil fabrication technique described below with reference to FIG. 4 facilitate wire-winding with winding pitch P of about 12-13 μm (e.g., for insulated wire having conductor's width of about ~10 μm coated with electric isolation/enamel-coating therebetween of about 2-3 μm).

These methods thereby enable achieving high winding count of the helical conductor of conductive winding arrangement CW per unit length of the core FC, for instance achieving winding count of about 100 to 150 windings per 1 millimeter of core length covered by the conductive winding arrangement CW per layer using the technique of FIG. 2 (typically about 125 windings/mm per layer), and winding count of about 77 to 83 per layer in the embodiment of FIG. 4. In both methods, the thickness of the conductor may be of the same order of magnitude as its width, or thicker (e.g., in the order of 4 μm or more) so as to facilitate sufficient conductivity and low resistance of the SMD-Coil although the narrow widths of the conductors. In some embodiments the thickness may be even larger, e.g., above 6 μm, in order to obtained further reduction in the coil's resistivity.

The above configuration of the helical SMD-Coil of the invention thereby results with compact dimensions and high inductance/induced-voltage SMD-Coil suitable for SMT installment in magnetic field positioning sensors suited for furnishing in catheters.

Figure 1B:
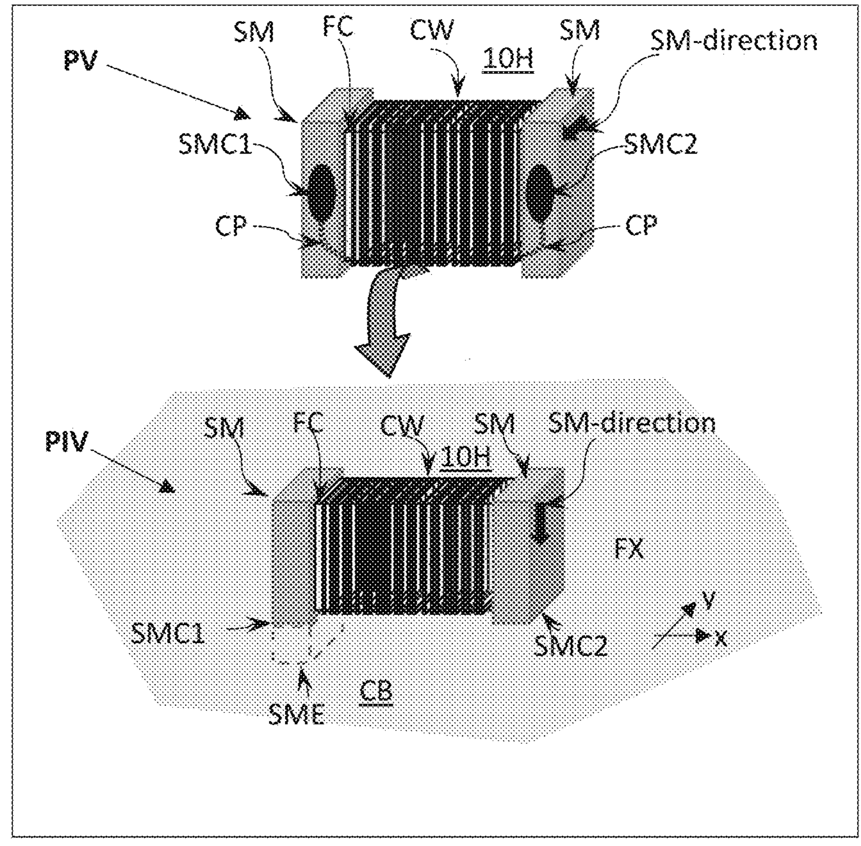
Figure 1C:
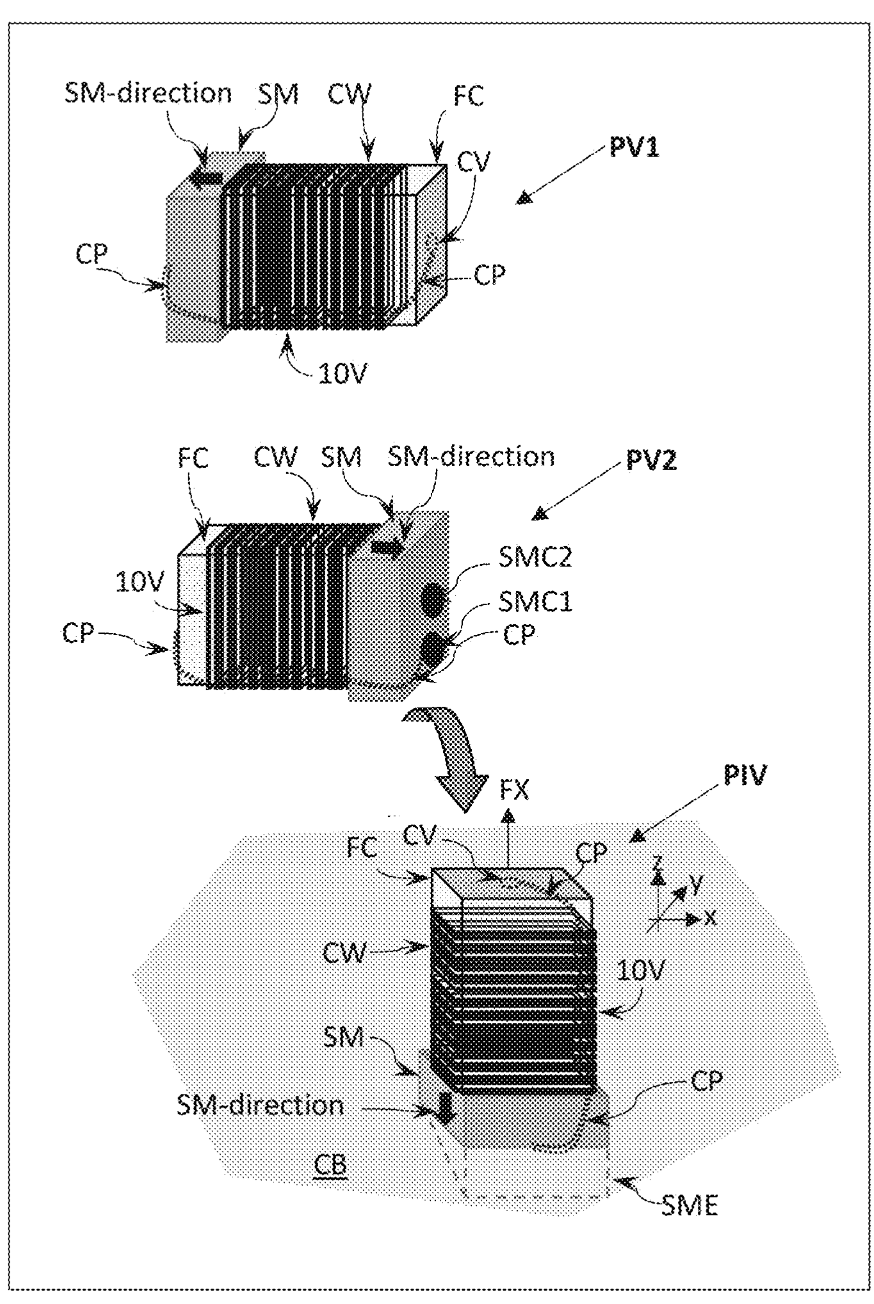

Reference is made now to FIGS. 1B and 1C in which perspective illustrations of two embodiments of the SMD-Coil 10 described above with reference to FIG. 1A are shown. FIG. 1B illustrates an embodiment 10H of the SMD-Coil 10 shown in FIG. 1A, which is configured for horizontal installation on a circuit board CB such that its longitudinal/magnetic-flux axis FX is substantially parallel to the surface of the circuit board CB (this embodiment 10H is also referred to hereinbelow as horizontal [helical-] SMD-Coil). FIG. 1C illustrates an embodiment 10V of the SMD-Coil 10 configured for vertical installation on a circuit board CB such that its longitudinal/magnetic-flux axis FX is substantially perpendicular to the surface of the circuit board CB (this embodiment 10V is also referred to hereinbelow as vertical [helical-] SMD-Coil). The figures also illustrate possible other configurations/extensions SMEs of the Surface Mount Portions SM of the SMD-Coil 10, which may be integral part of the Surface Mount Portions SM or extensions therefore, facilitate installation of the SMD-Coil 10 of the invention at any desired angle with respect to the surface of the circuit board CB. It should be understood that even if not specifically mentioned, the embodiments of FIGS. 1B and 1C described below may incorporate all or any suitable combination of the features of the SMD-Coil described above with reference to FIG. 1A.

Referring specifically to FIG. 1B, the figure shows a perspective view PV of the a helical SMD-Coil 10H according to an embodiment of the invention, which is configured for flat/parallel installation on a surface of a circuit board CB (or possibly at other orientations utilizing the optional Surface Mount configurations SME shown), as well as a perspective view of installation PIV illustrating how the orientation by which the SMD-Coil 10H is furnished on the circuit board CB. The surface mounting direction SM-Direction, pointing to the designated location of the circuit board CB with respect to the helical SMD-Coil 10H, is also illustrated in the figure.

In this embodiment the helical SMD-Coil 10H includes at least two SMT-Mounting Portions SM arranged from opposite ends of the Coil Portion C. Each of the two SMT-Mounting Portions SM includes at least one electric contact, SMC1 and SMC2, that is suitable for SMT installation on the circuit board CB. The two electric contacts SMC1 and SMC2 on the two respective SMT-Mounting Portions SM, are respectively electrically connected to the conductive winding arrangement CW from a opposite respective end thereof, for instance via an electrically conductive path CP arranged therefrom and on and/or through the respective SMT-Mounting Portion SM to contact the respective end of the conductive winding arrangement CW. Thus, in this embodiment the SMT electric contacts SMC1 and SMC2, which are electrically connect to respective end of the helical winding, reside on external faces of the SMT-Mounting Portion SM which are substantially parallel to one another and substantially parallel to the flux axis FX (e.g., 0° or at least less than 45° relative to the flux axis FX, depending on the SME configuration). Accordingly, the horizontal helical SMD-Coil 10H of this embodiment of the invention is particularly suited for surface mounting to a circuit board CB with its magnetic flux axis FX substantially parallel to the circuit surface, or at any other suitable angle with respect thereto (typically between 0° and) 45° according to the optional SME configuration.

Referring now to FIG. 1C, the figure shows two perspective views PV1 and PV2 of the a vertical helical SMD-Coil 10V according to an embodiment of the invention, which is configured for vertical/perpendicular installation on a surface of the circuit board CB (or possibly at other orientations utilizing the optional Surface Mount configurations SME shown), as well as a perspective view of installation PIV illustrating how the orientation by which the SMD-Coil 10V is furnished on the circuit board CB. The surface mounting direction SM-Direction, pointing to the designated location of the circuit board CB with respect to the helical SMD-Coil 10V, is also illustrated in the figure.

In this embodiment the helical SMD-Coil 10V includes at least one SMT-Mounting Portion SM arranged from an end of the Coil Portion C. The SMT-Mounting Portion SM includes at least two electric contacts, SMC1 and SMC2, that are suitable for SMT installation on the circuit board CB. The two electric contacts SMC1 and SMC2 on the SMT-Mounting Portion SM, are respectively electrically connected to the conductive winding arrangement CW from a opposite respective end thereof. For instance, one of the electric contacts SMC1 may be electrically connected to an end of the conductive winding arrangement CW proximal to the SMT-Mounting Portion SM it resides on, via an electrically conductive path CP arranged therefrom and on and/or through the SMT-Mounting Portion SM to contact the respective end of the conductive winding arrangement CW. The SMD-Coil 10V may also include a conductive element CV (conductive via or rod or wire) passing from the SMT-Mounting Portion SM at which it is connected to the second electric contact SMC2 and to the remote end of the Coil Portion C (distal from the SMT-Mounting Portion SM) at which it is connected to the remote end of the conductive winding arrangement CW. In embodiments, conductive element CV may be a conductive via/rode or wire passing through the magnetic core and insulated from the conductive windings thereover. In such embodiments a conductive path may optionally be fabricated-on/provided-at the remote end of the Coil Portion C to connect the conductive element CV to the remote end of the conductive winding arrangement CW. Alternatively, conductive element CV may be passing externally to the Coil Portion C to connect the second electric contact SMC2 to the remote end of the conductive winding arrangement CW. Thus, in this embodiment both the SMT electric contacts SMC1 and SMC2 which are electrically connect to respective end is of the helical winding, reside on the external face of the SMT-Mounting Portion SM which is substantially perpendicular to the flux axis FX (e.g., at 90° or at least between 45° and 90° relative to the flux axis FX, depending on the SME configuration). Accordingly, the vertical helical SMD-Coil 10V of this embodiment of the invention is particularly suited for surface mounting to a circuit board CB with its magnetic flux axis FX substantially perpendicular to the circuit surface, or at any other suitable angle with respect thereto (typically between 45° and) 90° according to the optional SME configuration.

Further to the above, with reference together to the embodiments of the SMD-Coil 10 described above in relation to FIGS. 1A to 1C, the following should be noted: Preferably, according in some implementations of the invention the conductive winding arrangement CW includes a helical conductor arrangement that is located directly on the magnetic core FC (e.g., with substantially no gaps therebetween). This configuration may be achieved by embodiments of the SMD-Coil fabrication methods 200 and 300 described below. Advantage of this configuration, for example over conventional configuration in which the core is inserted in post-production to the helix leaving residual gaps (e.g., air gap), is that the core occupies the full geometric cross-section at the center of the helical windings (with no gaps), thereby yielding higher sensitivity of the coils (higher induced voltage per magnetic field of given strength for the same size and number of windings).

Typically, in implementations of the present invention, the magnetic core FC of the SMD-Coils 10 has a tubular shape. In this regard it should be note that although in the specific non-limiting in the examples of FIGS. 1A to 1C the magnetic cores are illustrated with rectangular cross-sections, this cross-sectional shape was only provided as an example and in general any cross-sectional shape indicated above may be implemented in the magnetic cores of the SMD-Coils 10 without departing from the scope of the present invention.

Preferably, in some implementations of the SMD-Coils of the present invention the ferrite core has an elongated tubular shape so that the effective permeability of the core and therefore induced voltage is improved by the elongated core geometry. Alternatively, in some implementations where geometric constraints of the device in which the SMD-Coil prevent the elongated tubular core shape (e.g., for example in the case describe below of furnishing the vertical SMD-Coils 10V in the catheter), the ferrite core may be formed with flattened/squashed tubular shape and with a larger cross-section so as to compensated for the reduction in effective permeability of the core due to its flattened geometry.

Reference is now made to FIG. 2 which is a flow diagram illustrating a method 200 for fabrication of a helical SMD-Coil directly over a magnetic core according to an embodiment the present invention. More specifically the method 200 facilitates the fabrication of the helical conductive winding structure CW of the SMD-Coil 10 shown in FIGS. 1A to 1C, directly on a circumference surface of the magnetic core, and may also be used for fabrication of the suitable electrically conductive connection(s)/path(s) CP between the conductive winding structure CW and SMT contacts (SMC1 and/or SMC2) of the surface mounting portion(s) SM. This generally is achieved by utilizing photolithographic processes to form a pattern of the conductive windings on the magnetic core and then electroplating the conductive windings along said pattern. More specifically method 200 includes the following operations as described below.

In operation 210 a magnetic core FC having a tubular shape as defined above, is provided. Optionally, in embodiments of the method 200, the magnetic core FC provided may include, or be constituted by, sintered magnetic material having magnetic relative permeability u in the order of at least 100. Preferably in some embodiments of the present invention the magnetic core FC is substantially constituted by the magnetic core FC provided (e.g., with no substantial amounts of non-magnetic materials therein). Preferably for some applications and in some embodiment of the invention a magnetic core of material FC that is temperature stable in the temperature range of 20° C. to 60° C. is provided (e.g., with temperature coefficient of permeability of less than <160 ppm/° C.).

In optional operation 215 a seed layer may be fabricated over a circumference surface/section of the tubular magnetic core FC. This operation may be performed in case where the conductivity of the bare surface of the magnetic core FC is insufficient for electroplating. The seed layer may be fabricated by any suitable technique as will be appreciated by those versed in the art, for example by chemically applying a catalyst followed by thin electroless copper coat on the circumference surface/section of the tubular magnetic core FC to increase its electrical conductivity and facilitate the subsequent electroplating. Operation 215 is optional as in cases where the bare surface of the magnetic core is sufficiently conductive for electroplating, there may be no need for fabrication of the seed layer.

It should be noted that in various embodiments the operation 215 may be carried out at different stages of the method 200.

For instance, in some implementations of method 200 the catalyst is deposited selectively on the magnetic core FC and not deposited on the photoresist that is applied thereon in operation 220 described below. In such embodiments the operation 215 may be carried out only after the operations 220 and 230 described below for fabricating the seed layer at surfaces of the core FC from which the photoresist is removed by photolithography in operation 230. In such embodiments, the surface of the magnetic core under the photoresist will remain clean of both catalyst and seed layer and the electroless copper will grow substantially only on the exposed surfaces of the magnetic core, at which then the conductive windings will be formed by the electroplating (operation 240). In such embodiments, the optional operation 245 of removing of the remaining photoresists may be obviated as there was no forming of a conductive layer underneath it (note that actual removal of the photoresist may still be required depending on chemical and thermal stability of the photoresist used).

In some other example implementations of method 200 where the catalyst used remains active after application of photolithographic processes (UV light projection and photoresist developing solution), the operation 215 may be carried out in two stages:

- in a 1$^{st}$ stage of performed before the operations 220 and 230, the catalyst may be applied to the magnetic core FC;
- in a 2$^{nd}$ stage of performed after the operations 220 and 230 the seed layer may be fabricated at the exposed magnetic core regions of the pattern from which the photoresist is removed (the helix and possibly SMT flanges).

In both the above-described implementations (where the seed layer itself is applied after the photolithography of the photoresist and not underneath it) as well as in embodiments where there is no need for seed layer, the removal of the photoresists remaining after the patterning in optional operation 245 may be obviated, since a conductive layer will not be formed of underneath the photoresist. Yet in practice actual removal of the photoresist may still be performed in 245 depending on chemical and thermal stability of the photoresist used. Thus, in some implementations at which removal of the remaining photoresist is not necessitated, a permanent resist (similar to SU8 available as dry-film photoresist) may be used in operation 230 below.

In yet another example implementation (e.g., which may be carried out in case selective catalyst deposition is not facilitated and/or in case the catalyst does not remain active after the photolithography processes) the deposition of the catalyst and seed layer in operation 215 may be applied to the magnetic core prior to the application of the photoresist in operation 220. In this case a conductive layer will exist underneath the photoresist, and operation 245 will be required after the electroplating for stripping out the remaining photoresist and etching the seed layer in between the conductive windings electroplated in operation 240.

In operation 220 a photoresist layer may be applied to the circumference surface/section of the tubular magnetic core FC from all around (360°). Preferably the photoresist layer is applied with sufficient thickness (e.g., of at least 8 μm) in order to facilitate later application of relatively thick electroplating (e.g., at least 6 μm thick) at regions at which the photoresist layer will be removed by patterning, while without spillage/spread of the electroplated conductive material outside of the pattered regions. This may be advantageous to enable subsequent fabrication of relatively thick conductive windings of the coils having low electric resistance.

In this connection, optionally, in operation 220, a layer of dry photoresist may be used and may be applied all around (360°) the circumferences of said surface/section of the tubular magnetic core FC. The use of dry photoresist may be advantageous in this case as its application to the 3D circumference of said surface/section of the tubular magnetic core FC may be more controllable and uniform (e.g. in thickness) as compared to wet photoresists, and since it facilitates achieving substantially thick photoresist layer suitable for the subsequent fabrication of conductive windings having low resistivity and defined boundaries by electroplating (i.e. this facilitates electroplating of narrow conductive lines of the helical conductive windings with substantial thickness while preventing spread of the electroplating between adjacent lines and thereby facilitate small spacing between them, and thus fabrication of dense windings with small pitch P).

In operation 230 photolithography is applied to pattern the photoresist layer and form a helical pattern over said circumference surface/section of the tubular magnetic core FC which is covered by the photoresist layer. For instance, optionally, the photolithographic process may include the selective projection of photolithographic light of suitable frequency (e.g., UV light) having on the one hand sufficient power for patterning the photoresists, while on the other hand a power/intensity that is insufficient for causing damage to the underlying magnetic material of the core FC (so as not to damage the core and increase its conductivity).

The selective projection of the photolithographic light may be carried out by direct scanning of the laser beam on the circumference surface/section of the tubular magnetic core FC and/or by any other suitable technique as will be appreciated by those versed in the art of photolithography after knowing the present invention. It would be appreciated that optionally, in order to apply the photolithographic pattern over the three-dimensional (3D) circumference surface/section of the tubular magnetic core FC, the core may be rotated with respect to the light beam during the projection, while also shifting the magnetic core relative to the light beam (e.g., by moving the relative position of the core or by optical steering the light beam) along the longitudinal axis FX of the core. This may be done continuously or intermittently depending of the shape of the core's cross-section and the desired form of helical pattern to be produced. It should be noted that in embodiments of the present invention the photoresists used may be a so called "positive" photoresists or a "negative" photoresist, and the projected light pattern is adapted accordingly (as negative or positive pattern) so as to yield the desired helical pattern of exposed regions of the photoresist at which the conductive windings CW will be subsequently electroplated. As will readily be appreciated, the exposure of the photoresists is then followed by development of the photoresists to expose a helical pattern on the circumference surface/section of the tubular magnetic core FC, from which the photoresist is removed by said development.

Operation 240 includes electroplating the exposed regions of the magnetic core FC (the helical pattern formed after the development of the photoresist) with conductive material (e.g., copper) to yield said conductive winding CW in the form of a conductive helical coil over the external surface layer of the magnetic core. Preferably in some embodiments the electroplating is conducted to thickness in the order of about 4 μm or more.

In optional operation 245, which may be conducted after said electroplating, remaining photoresists material may be removed from between conductive windings of the helical coil CW. In this regard as indicated above in some implementations the surface conductivity of the magnetic core FC underneath the remaining photoresist material may be above a minimal desired threshold (e.g., due to for example a seed layer if such is fabricated in operation 215 before deposition of the photoresist layer). In such embodiments it may be desirable to reduce surface conductivity of the magnetic core FC in order to prevent electrically shorting between adjacent windings (and possibly also to suppress eddy currents from occurring during operation of the coil). To achieve that, in operation 245 the remaining photoresist may be removed from the core followed by etching of conductive seed layer/material and/or catalyst which may have been located between the photoresist and the magnetic core. This operation may be for example carried out in cases where the seed layer under the photoresist that needs to be removed in order to clear shorts across the helix. Regarding a threshold value, whether due to catalyst, seed layer or small intrinsic conductivity of the ferrite, the core resistance (whether due to volumetric or surface conductivity) must be larger about 100 times or more the coil (winding) resistance. Considering for example that the resistance of the helical windings from contact to contact is in the order of hundreds of Ohms, the resistance of the ferrite/magnetic core, flange to flange (solder contact to solder contact) should be in the order of tens of kilo Ohms.

Finally, preferably the helical SMD-Coil or the conductive windings parts thereof, which are fabricated by method 200, may be coated with a thin layer of varnish or tin coating for protection from oxidation of the conductive windings (e.g., during storage of the coils before assembly of the coils in a sensor/circuit at which time they might be further potted with epoxy for protection).

In some embodiments of the present invention a single winding layer may be fabricated by method 200 directly over the magnetic core FC. This may reduce fabrication complexity and costs, while still providing sufficient sensitivity due to the high density (small pitch) of the windings obtained by method 200 and the high core permeability. Alternatively, in some embodiments stacked/concentric windings layers may be fabricated by repeating the relevant operations of method 200 while introducing insulation material/layer between the successive conductive layer fabrication, as will be appreciated by those versed in the art.

In some embodiments of the present invention, method 200 may be adapted for fabrication of the conductive helical coil CW with high density windings, and wherein a pitch of the helical pattern and correspondingly of the windings in said conductive winding structure CW is in the order of, or less than 10 μm (preferably in some embodiments not exceeding about 8 μm). For instance, a width of conductive path forming the windings of said conductive helical coil may not exceed 7 μm (in some embodiments not exceeding 4 μm) and a spacing between conductive paths of adjacent windings is in the order of 4 to 5 μm so as to provide high-density windings over said ferrite core.

As indicated above according to some embodiments of the present invention, the operations of method 200 may be carried out in order to also fabricate suitable electrically conductive connection(s)/path(s) CP between the conductive winding structure CW and SMT contacts (SMC1 and/or SMC2) of the surface mounting portion(s) SM of the SMD-Coil 10 of the invention. To this end, in operation 210, the ferrite core FC may be provided furnished with the Surface Mount Portion(s) SM, accordingly optional operation 215 and operation 220 to 240 may be carried out in a similar manner as described above in order also to fabricate the electrically conductive connection(s)/path(s) CP between the conductive winding structure CW and SMT contacts (SMC1 and/or SMC2) of the surface mounting portion(s) SM. For example, in embodiments of the vertical SMD-Coil 10V, operation 220 to 240 may be carried out to define the two electric contacts SMC1 and SMC2 on the same mounting portion(s) SM without electrically shorting them. Additionally, in some embodiments where SMD-Coil 10V of the vertical installation is fabricated, the magnetic core FC may be provided with a through conductor CV passing across it generally along its longitude axis FX, and one of the conductive paths CP may be fabricated with the through conductor CV incorporated as part thereof as exemplified in optional markings in FIG. 1C.

Alternatively, or additionally, in some embodiments method 200 with the operations described above, may be adapted mainly to the fabrication of the coil portion C of the SMD-Coil 10 and the attachment between the coil portion C and surface mounting portion(s) SM and/or the electrical coupling between the conductive winding structure CW of the coil portion C and the SMT contacts (SMC1 and/or SMC2) on the surface mounting portion(s) SM may be performed in a separate process.

Reference is now made to FIG. 3 in which an example of a fabrication system 280 according to an embodiment of the present invention is illustrated. The fabrication system 280 is configured and operable for implementing at least the operation 230 of method 200 described above, so as to apply photolithography over a magnetic/ferrite core FC to which photoresist was applied, to form a helical photoresist pattern suitable for fabrication (e.g., electroplating) of helical conductive windings directly over the magnetic core FC. The fabrication system 280 includes a photolithographic light-source LS, such as a UV laser light source with the properties exemplified above, which is suitable for projecting light LL towards the magnetic core FC to apply photolithography to a photoresist layer on the magnetic core FC. The fabrication system also includes a handler utility HL which is configured and operable for carrying/holding the ferrite core and applying relative movement between it and the light LL from the photolithographic light-source LS to project (e.g., sequentially), a helical winding pattern on the magnetic core FC. For instance, the helical pattern may be projected utilizing a combination of relative rotational movement RM about axis RX and linear movement LM parallel to said axis RX, which may be affected by the handler utility HL (or optical steering of the laser beam) between the magnetic core FC. Accordingly, the handler utility HL and a control unit CU of the fabrication system 280, which is adapted for controlling the handler utility HL and the light-source LS, may are configured and operable to apply such relative movement between the magnetic core FC and the photolithographic light-beam LL so as to project a three-dimensional helical pattern of the photolithographic light on the core.

Reference is made to FIG. 4 in which a flow diagram of another method 300 for fabrication of the coil portion C of a compact SMD coil 10 according to an embodiment of the invention is provided. More specifically, method 300 is adapted to fabricate a helical coil directly on a magnetic core FC by winding a wire over a circumference the magnetic core.

In operation 310 of method 300 a magnetic core FC having a tubular shape is provided. Optionally, in some embodiments the magnetic core FC may include, or be constituted by, sintered, or more preferably fully-sintered magnetic material having magnetic permeability u in the order of at least 100. In some embodiment a magnetic core FC of material that is temperature stable in the temperature range of 20° C. to 60° C. is provided (e.g., with temperature coefficient of permeability of less than <160 ppm/° C.).

Optionally, in embodiments of vertical installation configuration of the SMD-Coil 10 as shown in FIG. 1C, the magnetic core FC may be provided with a through conductor CV passing through it (generally along its longitude axis FX) from a first end thereof to an opposite end, for conductively connecting surface mount connector SMC of a Surface Mount Portion SM to be located at said opposite end with an end of the helical coils/conductive-windings CW proximal to said first end (this is optional as alternatively an external conductor may be used for this purpose without substantially impairing the functioning of the coil).

It is noted that sintered magnetic cores are typically relatively brittle and may be relatively easily damaged under the pressure/tension applied thereto in the process of wire windings. Therefore, in some embodiments optionally in order to facilitate mechanical endurance of the magnetic core during the wire-winding, the magnetic core provided, may have a round cross section in the center section which is wound (so as to relieve stress from the wounded wire) while the flange regions may have polygonal/rectangular cross-sections) that the magnetic core is capable of enduring stresses applied thereto by the conductive wire during its winding without substantial damage.

Alternatively, or additionally, as indicated in optional operation 320, in some embodiments prior to the wire winding, one or more surface regions of the magnetic core are coated/coupled with a buffer layer/structure of material suitable for relieving mechanical stresses from the magnetic core itself and/or from the wire winded thereon. For instance a layer of flexible material such as wax capable of absorbing/mitigating/distributing some of the stresses applied between the core and the thin wire during the winding (thereby preventing both damage to the core as well as breakage of the wire during the winding) or a structurally enforcing material such as polymer, for example coating surfaces of the magnetic core, or provided as "pillars" in corners of the magnetic core (in case its cross-section is polygonal) to absorbed/distribute some of the stresses applied between the core and the thin wire. In some embodiments the buffer layer or structure need not be removed after the winding processes (e.g., thereby not potentially forming any gaps between the windings and the core. Alternatively, in other embodiments, the material may be removable/removed from the core after the wire winding.

In operation 330 a thin conductive wire (e.g., of characteristic width of about 10 μm and less than 20μ) is provided and winded over the magnetic core to form said conductive winding structure. The windings may be performed with one or more layers of winded wires thereby forming a single helical wire structure, or a structure of multiple concentric helixes of wire, over the circumference of the magnetic core.

Typically, the winding of the horizontal helical SMD coils 10H is performed with an odd number of winding layers so that the two ends of the winded wire land on opposite ends of the core to be connected to metallized/contact areas there. Accordingly, typically the winding of the vertical helical SMD coils 10V is performed with an even number of layers so that the two ends of the wire land on the bottom face of the core (which is to be installed on the circuit board). In this case each end of the wire is attached to a different metallized contact pad on the SMT mount of the bottom face core (with no need to pass the wire through a drill of the ferrite core or externally to the coil).

Preferably, winding is performed while mitigating the tension applied on the winded wire so as to prevent tearing of the wire (for example when utilizing conductive wire of 10 μm in diameter, the maximum tension applied to the wire during the winding does not exceed about 1.4 g.

Thus, embodiments of method 300 are adapted to fabrication of a coil portion C of the SMD-Coil 10 of the present invention. In this regards it should be noted method 300 as described above is specifically suited for the fabrication of conductive windings utilizing thin conductive wire of characteristic diameter/width in the order of 10 micrometers and less than 20μ while mitigating pressure/stress applied by the wire on the magnetic core and relieving tension from the wire so as to eliminate or at least reduce and control any damage which may be affected on the magnetic core by the wire-winding process and also prevent/reduce tearing of the winded conductive wire during the process. For example, 10 μm diameter copper wire (e.g., 12-13 μm including enameled wire insulation), or even thinner wire, may be winded directly over the core with for example few hundred turns (e.g., 600) in one or more layers.

In view of the above method 300 thereby enables high fabrication throughput of high-density direct winding of thin conductive wire over the magnetic core while with reduced waste/production of damaged-products. In some implementation the method 300 may also implemented for automated/fully automated production of compact coils, Accordingly, a robust method is provided for fabrication of SMD-coils having robust SMT contacts (which are more reliable than soldering wires)

Methods 200 and 300 described above, is generally supplemented by the attachment/furnishing of one or more Surface Mount Portion(s) SMs from one or both ends of the magnetic core FC and electrical connection of their contacts to the coil. In order to avoid interference of the Mount Portions SMs with the operation of the coil C, the Surface Mount Portions SMs may be formed with non-ferromagnetic material (e.g., copper and/or tin) and/or possibly from Nickel, which although being ferromagnetic, may in some cases be used depending on the specific design of the magnetic core and nickel coating used. In various embodiments the attachment of the Surface Mount Portions SMs the operation may be conducted prior-to the implementation of method 200 or 300 by which the conductive winding structure CW of the coil portion C is fabricated. Alternatively, or additionally, with the implementation of method 200, the attachment of the Surface Mount Portions SMs and/or their electrical connection to the coil may also be conducted during or after the implementation of the method.

Reference is now made together to FIGS. 5A to 5D, 6A to 6D, 7A to 7D and 8A to 8D, illustrating several embodiments of a position sensor 100 according to the present invention, which is adapted to measure signals indicative of at least one of a location and orientation of the sensor relative to a magnetic field source. The position sensor 100 in each of these embodiments includes a flexible circuit board CB (e.g., foil circuit board or flex PCB or any other suitable flexible circuit surface as will be appreciated by those versed in the art suitable for use with the sensor of the present invention), and at least three helical SMD-coils surface-mounted to the circuit board CB with surface mount technology (SMT). The flexible circuit board CB is folded to an operative configuration at which the at least three helical SMD-coils are arranged such that their magnetic axes FXs are not co-planarly arranged thereby enabling the at least three helical SMD-coils to sense different aspects of a designated external magnetic field, which are indicative of at least one of a location and orientation of the sensor 100 relative to the external magnetic field (i.e., relative to an external magnetic field source). Accordingly, the signals obtained from the at least three SMD coils are utilized to measure/assess at least one of the orientation and location of the sensor 100 relative to one or more magnetic field sources.

For brevity FIGS. 5A to 5D, 6A to 6D, 7A to 7D and 8A to 8D, which exemplify various embodiments of the sensor 100 of the present invention, depict as follows in self-explanatory manner: the figures numbered FIGS. #A (i.e. FIGS. 5A to 8A) provide schematic perspective view illustrations showing respective flat/planar circuit layouts of the position sensor 100 according to several embodiments of the present invention in which corresponding arrangements of SMD-Coils 10 are shown surface mounted to a flexible circuit CB (the perspective circuit layout views are shown in FIGS. 5A to 8A at a state where the surface of the flexible circuit CB is flat, i.e. before the flexible circuit CB is folded/rolled to yield the operative configuration of the sensor); The figures numbered FIGS. #B (i.e. FIGS. 5B to 8B) provide schematic side-view illustrations of the position sensor 100 corresponding to the respective embodiments of the sensor shown in FIGS. 5A to 8A; and The figures numbered FIGS. #C (i.e. FIGS. 5C to 8C) and FIGS. #D (i.e. FIGS. 5D to 8D) are schematic front-view illustrations showing a cross-section of the position sensor circuit as viewed from along a longitudinal axis thereof, after the flexible circuit CB is folded/rolled about respective folding axes FAi and FAo to form the operative configuration of the sensor 100, whereby the figures numbered FIGS. #C illustrate embodiments in which the flexible circuit CB is folded such that the coils are located at the outer surface of the folded flexible circuit CB, and the figures numbered FIGS. #D illustrate embodiments in which the flexible circuit CB is folded such that the coils are located at the inner surface of the folded flexible circuit CB.

In this regard FIGS. 5A to 8D exemplify two optional folding axes FAi and FAo about which the circuit board CB may be folded such that it is formed in a tube-like structure. In some embodiments, as illustrated for example in FIGS. 5C, 6C, 7C and 8C the circuit board CB may be folded about a folding axis is FAo to a tube-like structure (open or closed), with the sensor coils 10 arranged on the outer surface of the tube-like structure of the folded circuit board CB. In such embodiments for example the circuit board CB may be folded/rolled into tube of inner diameter less than 1 mm, preferably even less than 0.9 mm. In this case the circuit board CB may be for example foil circuit of thickness of about 10 to 50 microns (e.g., foil of thickness of 0.0127 mm) having printed conductive-tracks/connections CC and solder pads upon which the SMD coils of the sensor can be mounted and soldered). In some embodiments, as illustrated for example in FIGS. 5D, 6D, 7D and 8D the circuit board CB may be folded about a folding axis is FAi to a tube-like structure (open or closed) such that the sensor coils 10 are arranged on the inner surface of the tube-like structure of the folded circuit board CB. For clarity, in the following the folding axis, be it FAi or FAo, about which the circuit board CB is folded is also considered and referred to as the longitudinal axis of the sensor 100.

For brevity, in the non-limiting examples of the position sensor 100 provided in FIGS. 5A to 8D the at least three helical SMD-coils shown to be disposed with angular intervals of 60° or 120° between them with respect to the designated folding axis is FAo or FAi. It should be however understood that these angular intervals are provided herein only as an example and that in various embodiments of the present invention the at least three coils may be arranged with other angular intervals between them (e.g., possibly with interval of 90°, and/or with different/varying angular intervals between them, while still being operative to sense the position and/or orientation of the sensor relative one or more magnetic field sources. In this regard it will be appreciated that the sensor 100 may generally be configured with angular intervals of the coils different than those illustrated in the figures in order for example to accommodate various design constraints such as compact/desired arrangement of the coils 10 and/or reducing/adjusting mutual sensing of common magnetic-field signal components by different coils.

Referring now specifically to the example embodiments of the position sensor 100 shown in FIGS. 5A to 5D, the sensor 100 adapted to measure signals indicative of location and/or orientation thereof relative to a magnetic field source MFo. In this embodiment the at least three SMD coils 10 may for example include three horizontal helical SMD coils 10H configured according to the embodiment of the present invention that is described above in relation to FIG. 1B. To this end, the three SMD coils 10H may be surface mounted to the surface of the circuit board CB via surface mount technology.

In various embodiments the position sensor 100 of FIGS. 5A to 5D is specifically designed to facilitate utilization of the signals obtained from these three SMD coils to determine the orientation of the longitudinal axis FAi or FAo of the sensor 100 relative to the magnetic field source MFo whereby the magnetic field source MFo is generally located in front of the sensor 100 along a general direction of the longitudinal axis FAi or FAo of the sensor 100. The signals obtained from the three SMD coils 10H facilitate to determine the orientation relative to the magnetic field source MFo with respect to two angles (i.e., pitch and yaw) about the longitudinal axis of the sensor 100. To achieve that with accuracy, the three SMD coils 10H may be furnished on the circuit board CB with parallel orientation of their magnetic flux axes FXs relative to the surface of the circuit board CB, and such that their magnetic flux axes FXs are substantially parallel to one another. Preferably to facilitate accurate orientation measurements, the three SMD coils 10H are arranged on the circuit board CB such that they (specifically their core sections C) are alighted/justified with respect to straight guideline GL perpendicular to the longitudinal/folding axis FAi or FAo, and such that their magnetic flux axes FXs are substantially parallel to the longitudinal/folding axis FAi or FAo. Accordingly, when the circuit board CB is flexed/folded about the folding axis FAi or FAo to its designated operative configuration, the magnetic flux axes FXs of the three SMD coils 10H are substantially parallel to one another while not being co-planar (so as to facilitate orientation measurements about two angle), and preferably all three SMD coils 10H are (specifically their core sections C) are aligned with respect to a common reference plane RP (the reference plane may be for example the plane accommodating the guideline GL when the circuit is folded). Preferably, in some embodiments the at least three helical SMD coils 10H, which are used in the embodiments of FIGS. 5A to 5D to measure the orientation with respect to the magnetic source MFo, are coils of similar configuration (dimensions and inductance/reactance values).

Accordingly, the position sensor 100 of FIGS. 5A to 5D is suitable configured for accurate measurement of the orientation of the sensor relative to magnetic field source MFo positioned generally in front of the three helical SMD coils 10H of the sensor. Thus, by accounting the voltages induced by each of the SMD-coil(s) 10H, a signal processing circuit (not specifically shown; e.g., a computerized system) which may be connected to the sensor, may operate to determine the measured orientation of the magnetic field source MFo. For example, a compact helical SMD coils 10H configured according to the present invention with longitudinal dimension of the core section C extends about 1.2-1.4 mm (and totally about 2 mm together with the surface mounting portions), and lateral dimensions (width/diameter) extending in the order of 0.6 mm or less and more preferably in the order of 0.5 mm, and may yield sensitivity of about ~0.2 μV/(Gauss*Hz) thereby enabling accurate measurements of the orientation relative to the magnetic field source MFo. A person of ordinary skill in the art would readily appreciate various techniques for utilizing the signals obtained from the SMD-coils 10H of the sensor 100 of FIGS. 5A to 5D to determine/assess the orientation of the magnetic field source MFo relative thereto.

Referring now specifically to the example embodiments of the position sensor 100 shown in FIGS. 6A to 6D, the sensor 100 is adapted to measure signals indicative of location and/or orientation thereof relative to a magnetic field source $MF_L$. In this embodiment, the sensor 100 includes a flexible circuit board CB and three SMD coils whereby: two of the at least three SMD coils 10 are vertical helical SMD coils 10V configured according to the embodiment of FIG. 1C and surface mounted to the surface of the circuit board CB via surface mount technology with vertical/perpendicular orientation of their magnetic flux axes FX relative to the circuit board CB, and one SMD coil of the at least three SMD coils 10 is a horizontal helical SMD coil 10H configured according to FIG. 1B and surface mounted to the surface of the circuit board CB via surface mount technology with horizontal orientation of its magnetic flux axis FX relative to the circuit board CB. The three SMD coils 10 are arranged on the circuit board CB such that when the circuit board CB is flexed/folded/rolled about the folding axis FAi or FAo to its designated operative configuration (as exemplified in FIGS. 6B to 6D), the magnetic flux axes FXs of the three SMD coils 10 are not parallel to one another and span three dimensional coordinates which enable the coils to measure different vectored components in of a magnetic field in their vicinity. More specifically for example the two vertical helical SMD coils 10V may be arranged such that when the CB is flexed to its operative state their magnetic flux axes of said two SMD coils are not parallel and are for example in 90° or 120° with respect to one another, and the horizontal helical SMD coil 10H may for example be arranged with its magnetic flux axis relative being parallel to the folding axis FAi or FAo of the circuit board (e.g. optionally in some implementations this may facilitate compact folding of the circuit board).

To this end the arrangement of the at least three SMD coils 10 with their magnetic flux axes FX spanning three-dimensional coordinates facilitate the measurement of the vector component of magnetic fields in their vicinity thereby enabling to determine the location and/or orientation of the sensor 100 relative to an external source of magnetic field(s) $MF_L$. Generally, for example by utilizing external source of magnetic field(s) $MF_L$ generating a plurality of distinguishable magnetic fields (e.g., typically at least three magnetic fields of different frequencies) both the position and orientation of the sensor 100 may be determined. A person of ordinary skill in the art would readily appreciate various techniques by which the location and/or orientation of the magnetic field source $MF_L$ relative to the sensor 100 may be determined based on the measurement of the magnetic field vector components at the sensor 100

Preferably, in some embodiments the two vertical helical SMD coils 10V, which are used in the embodiments of FIGS. 6A to 6D may be coils of similar configuration (dimensions and inductance/reactance values). In some embodiments the vertical helical SMD coils 10V are configured with a core cross-section that is elongated in one lateral dimension (such as a core with elliptical cross-section or rectangular cross-section in which one lateral dimension is larger than the other as exemplified in FIG. 6A), and vertically furnished on the circuit board CB such of the longer side of their core cross-section is substantially collinear with the folding axis FAi or FAo about which the circuit board CB is to be flexed. This facilitates to have these coils with a sufficiently large cross-section so as to yield desired sensitivity of the position sensor, while on the other hand enables compact folding of the circuit board CB and thereby compact dimensions of the sensor, as only the shorted lateral dimension of the core is perpendicular to the folding axis and the larger lateral dimension is aligned with the folding axis and this does not limit the diameter of the circuit board folding. Accordingly, the position sensor 100 of FIGS. 6A to 6D is suitable configured for accurate measurement of the location and/or orientation of the sensor relative to a magnetic field source $MF_L$. For example, an SMD-Coil 10V configured with compact configuration according to the present invention and having longitudinal dimension extends about 0.45 mm to 0.6 mm (typically about 0.5 mm or less) along its magnetic axis and with elongated/elliptic cross-section having lateral dimensions of about 0.7 mm×2.2 mm may yield sensitivity of about 0.1 to 0.2 μV/(Gauss*Hz)) for sensing magnetic fields in the KHz frequency regime, thereby enabling accurate measurement of the location and orientation of the magnetic field source $MF_L$ (note that the measure of sensitivity is indicated here for uniform magnetic fields, and the sensitivity for non-uniform fields may be less).

Reference is now made together to the embodiments of the position sensor 100 illustrated in FIGS. 7A to 7D and 8A to 8D. In these examples the position sensor 100 includes at least five SMD coils 10, which are surface mounted on one or more flexible circuit boards CB (only one circuit board is illustrated in the non-limiting example shown in the figures). Three SMD coils of the at least five SMD coils 10 of the sensor 100 may be horizontal helical SMD coils 10H, which may be configured and arranged on the circuit board CB in a similar manner as described above with relation to FIGS. 5A to 5D (e.g., such that their magnetic flux axes FXs are parallel to one another and are not co-planar when the circuit board CB is furnished at the sensor in its folded/rolled operative state). Additionally, two SMD coils of the at least five SMD coils 10 of the sensor 100 may be vertical helical SMD coils 10V, which may be configured and arranged on the circuit board CB in a similar manner as the vertical helical SMD coils 10V described above with relation to FIGS. 6A to 6D (e.g. such that their magnetic flux axes are not parallel to one another, e.g., in 90° or 120° with respect to one another, when the circuit board CB is furnished at the sensor in its folded/rolled operative state and also not parallel to the magnetic flux axes FXs of the three horizontal helical SMD coils 10H of the sensor 100). This configuration thereby enables to utilize signals obtained from the three horizontal SMD coils 10H to determine two angles of orientation (e.g. pitch and yaw) of the sensor 100 relative to a first magnetic field source MFo (e.g. which may be located in-front of the three horizontal helical SMD coils 10H along a general direction of their magnetic flux axes, and operate to generate magnetic field of a first frequency such as 16 KHz), as well as utilizing the signals obtained from the two vertical helical SMD coils 10V together with signals obtained from any one (or more) of the horizontal SMD coils 10H to determine the orientation and/or location of the sensor 100 relative to a second magnetic field source $MF_L$ (e.g. which may operate to generate magnetic field of a second frequency such as between 1 and 4 KHz).

As shown in self-explanatory manner in the embodiments of FIGS. 7A to 7D and 8A to 8D, while satisfying the above-described configuration, the at least five SMD coils 10 may be arranged with various arrangements on the one or more circuit boards CB of the sensor in order to accommodate different prerequisite compact dimensions of the sensor, while packing therein the highly sensitive coils. For instance, in the embodiment illustrated in FIGS. 7A to 7D a sensor 100 of specifically narrow tubular shape is provided packing said five SMD-coils 10. In this example the three horizontal helical SMD coils 10H are arranged in a first row (e.g. aligned to the guideline GL) of the sensor 100, and the two vertical helical SMD coils 10V may not be arranged in the same row (e.g. may be arranged on the circuit board(s) CB backward from the row of the three horizontal helical SMD coils 10H) so that a circumference of the circuit board CB needs to accommodate the three horizontal helical SMD coils 10H at one circumference region, and at separate circumference region(s) to accommodate said two vertical helical SMD coils 10V. Thus, in this case as shown in FIGS. 7C and 7D, in the folded state of the circuit board(s) CB, the cross-sections of the three horizontal helical SMD coils 10H may overlap with the cross-sections of the two vertical helical SMD coils 10V, which therefore allows for compact folding of the circuit board(s) CB. Accordingly, a specifically narrow configuration of the sensor may be provided in this case. For example, in some embodiments the circuit board CB may be of about 12-15 μm in thickness and with longitudinal dimension of about L≈10 mm and width of about W≈2.5-3 mm and may be rolled to a tube-like shape of diameter about 1 mm or less.

Alternatively for instance, in the embodiment illustrated in FIGS. 8A to 8D a sensor 100 of specifically short longitudinal dimension may be obtained. In this example all the SMD coils 10 are generally arranged in on the circuit board a single row so that a short dimension of the sensor is obtained as shown for example in FIG. 8B.

With reference together to the sensors 100 illustrated in FIGS. 5A to 8D, the following should be noted:

In embodiments for example the three coils 10H, which are used to determine the orientation relative to the first magnetic field source MFo, may be similar coils or rectangular circular or elliptic cross-section, and the two additional coils 10V, which may be used together with one of said three coils, to determine the orientation/location relative to the second magnetic field source $MF_L$, may be similar or different, and may typically be of elongated cross section (e.g. elongated along the longitudinal axis of the sensor) such as having elongated rectangular cross-section or elliptic cross-section. It will be appreciated that although all the coils 10 of the sensors 100 in the above examples are considered to be surface mountable coils (e.g., SMD-coils configured according to the embodiments of the present invention as described in FIGS. 1A to 1C), in other implementations of the sensor 100 contemplated by the inventors, some of the coils may be not SMD-Coils and/or not configured according to the coil configuration described in FIGS. 1A to 1C. For instance, in embodiments the three coils, which are used to determine the orientation relative to the first magnetic field source MFo may be SMD-coils configured according to the present invention and the two additional coils which are used to determine the location/orientation relative to the second magnetic field source $MF_L$ may optionally be coils of other types, such as air-core coils.

To this end, it will be appreciated that the sensor 100 may be connected to a signal processing circuit (not specifically shown) which may include for example an external analog and/or digital processing circuitry adapted for processing the signals of the SMD-coil(s) 10 to determine the orientation of the sensor relative to the magnetic field source MFo and/or the location/orientation of the sensor relative to the second magnetic field source $MF_L$.

Figure 9A:
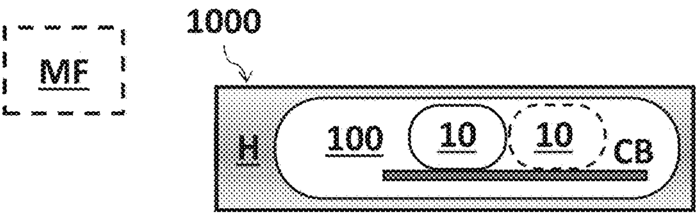
FIGS. 9A, 9B and 9C are schematic illustrations of medical instruments/devices incorporating a position sensor, according several embodiments of the present invention.

Reference is now made to FIG. 9A in which a block diagram of a medical instrument 1000 (e.g., probe/catheter) according to an embodiment of the present invention is illustrated. The medical instrument 1000, which may be a compact invasive medical instrument, generally includes a housing H and a magnetic field-based position sensor 100 configured according to the present invention and fixedly furnished at the housing H. The medical instrument 1000 is also associated with at least one magnetic-field source MF that is configured and operable for generating a designated magnetic field in its surroundings to enable the magnetic field-based position sensor 100 to determine at least one of its location and orientation relative to the at least one magnetic-field source MF. It is noted that in various embodiments at least one magnetic-field source MF may or may not be enclosed in the housing H and may or may not be integral part of the medical instrument 1000. As will be appreciated from the below description, in some embodiments the medical instrument 1000 is associated with several at least one magnetic-field sources MF generating magnetic fields of different properties (e.g., different frequencies) so as to enable measurement of the relative positions of orientations of different parts of the medical instrument 1000. According to the invention the magnetic field-based position sensor 100 is configured according to the invention as described for example in any of the embodiments of FIGS. 5A to 8D, and includes one or more SMD-Coils 10 (typically a plurality) surface mounted on a flexible circuit board CB which is arranged within the housing in its operative configuration in which it is flexed/folded/rolled as described above such that the magnetic flux axes of the one or more SMD-Coils 10 are not coplanar. Accordingly in this configuration a highly sensitive and compact position sensor 100 is contained withing small dimensions of the medical instrument.

Figure 9B:
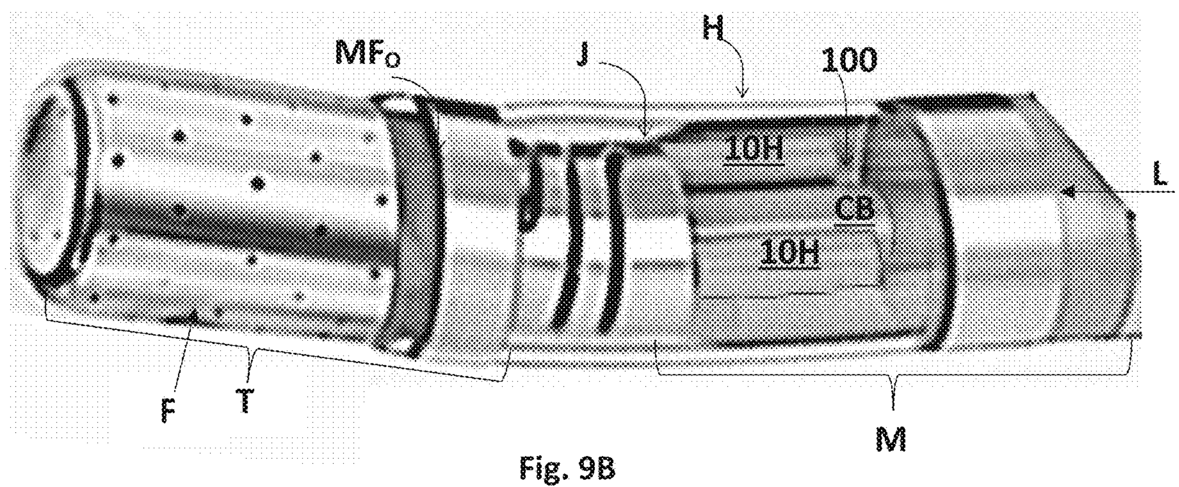

Reference is now made to FIG. 9B in which a perspective view of a medical instrument 1000 (e.g., probe/catheter) according to an embodiment of the present invention is schematically illustrated. The medical instrument 1000 in this embodiment is exemplifies a configuration of the medical instrument described above with reference to FIG. 9A in which the housing/medical instrument includes a main section M having a longitudinal axis L and a tip section T that is flexibly coupled to at a distal end of the main section M via a banding coupler J, such as a spring or joint, configured such that the orientation of the tip section T can be bent relative to the longitudinal axis L of the housing under applied force F (which may be applied for example when tip section T of the medical instrument is in contact with a body tissue of a patient) to degrees in correspondence with a magnitude and direction of the applied force F. In this example the medical instrument 1000 includes the magnetic field source MFo, which may be for example a coil associated with appropriate circuitry for generating a magnetic field. The magnetic field source MFo is typically fixedly located at the tip section T and the magnetic field-based position sensor 100, which is typically located within the main section M of the housing (it is noted that in some embodiments an opposite configuration where the magnetic field source MFo may be located at the main section and the position sensor 100 at the tip may be implemented depending on design/dimension constraints of the medical instrument). The magnetic field source MFo is configured and operable to generated a magnetic field provides a reference frame indicative of the orientation and possibly also the location of the housing section in which it is furnished (hereinafter and without loss of generality the tip section T). The magnetic field-based position sensor 100, which is located in another body section (hereinafter and without loss of generality the main section M) which is movable (e.g. rotatable) with respect to the section at which the magnetic field source MFo is located (e.g. with respect to the tip section T) is configured and operable for sensing the magnetic field generated by the magnetic field source MFo and based on said measurements determine/estimate the orientation of the tip section T relative to the main section M, which is generally indicative of the force vector F applied to the tip section (e.g. between the tip and a body tissue when the medical instrument is employed in medical operation).

To this end the magnetic field source MFo may be for example a coil arranged in the tip section T and generating an alternating magnetic field for example with frequencies in the KHz regime (e.g., 16 KHz). In embodiments for example, the coils of the magnetic field source MFo may be arranged such that in a neutral un-bent position of the tip section T relative to the longitudinal axis L of the housing, its magnetic flux axis is substantially colinear/coincides with the longitudinal axis L of the housing. The magnetic field-based position sensor 100 is position sensor 100 configured according to the present invention for example the position sensor illustrated in any one of the embodiments of FIGS. 5A to 5D, 7A to 7D and 8A to 8D in which at least three SMD coils are arranged such that their magnetic field axes are substantially parallel and not coplanar. This, as described above for example with reference to FIGS. 5A to 5D enables the measurement of the orientation of the sensor 100 relative to the magnetic field source MFo about to orientation angles (e.g., pitch and yaw), while utilizing the highly sensitive compact and reliable SMD-coils 10 of this purpose. In this example, as shown in the figure three horizontal helical SMD-Coils 10H are arranged in the sensor 100 (only two are visible in the figure) over the folded/rolled flexible circuit board CB to provide a compact sensitive and reliable sensor configuration.

To this end, having considered the technique of the present invention person of ordinary skill in the art will readily appreciate how said orientation of the sensor 100 relative to the magnetic field source MFo may be determined based on measurements of the magnetic field generated by the source MFo (which provides a reference frame relative to which the orientation can be determined). Moreover, a person of ordinary skill in the art will readily appreciate how said force vector F may be determined based on the measured orientation and the properties (e.g., spring constant) of said banding coupler J.

Figure 9C:
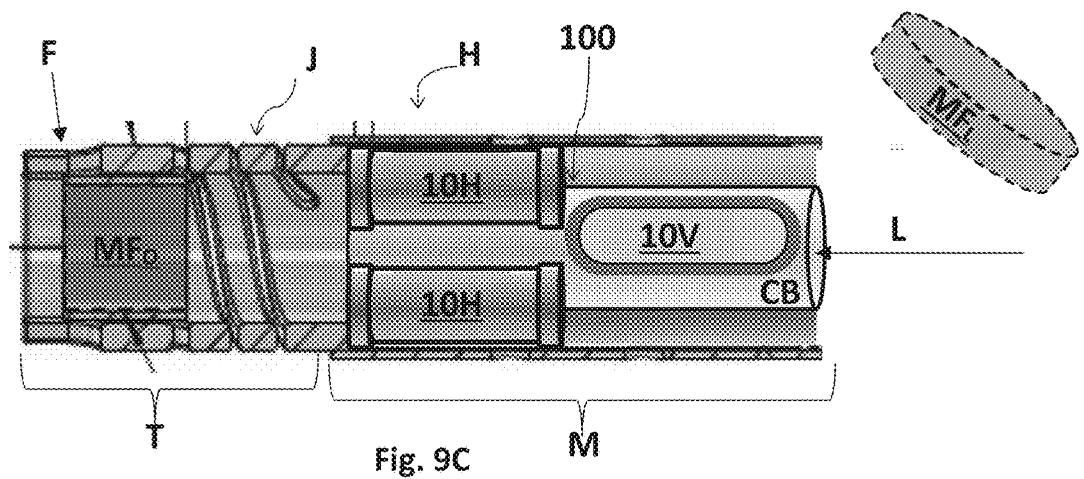

Reference is now made to FIG. 9C in which a side-view of a medical instrument 1000 according to another embodiment of the present invention is schematically illustrated. The medical instrument 1000 in this embodiment incorporates the features of the medical instrument 1000 which reference to FIG. 9B for determining the orientation of the tip section relative to the its main section (e.g., or determine the force applied on the tip) and is also adapted to determine/measure the spatial location and/or orientation of the medical instrument 1000 itself. To this end the medical instrument 1000 includes a magnetic field based position sensor 100 of the invention in which at least five coils are included, and is associated with another magnetic field source $MF_L$ which is to be located externally to the medical instrument 1000 and configured and operable for generating a second magnetic field, which is distinct from the magnetic field produced by the magnetic field source MFo (e.g. in frequencies) and which provides a spatial reference frame with respect to which the location and/or the orientation of the medical instrument 1000 may be determined (for example the magnetic field source $MF_L$ may be adapted to generate magnetic fields in two or more frequencies distinct from the frequency of the magnetic field source MFo to thereby enable determination of both the location and the orientation of the medical instrument 1000. The medical instrument 1000 in this embodiment may include a position sensor 100 of the present invention, such as that illustrated in any one of the embodiments of FIGS. 7A to 7D and 8A to 8D in which at least five coils/SMD-Coils are included. Accordingly, as described above with reference to these figures, a subset of at least three of these at least five coils may be arranged such that their magnetic flux axes span three-dimensional coordinates thereby enabling to determine a spatial location and/or orientation of medical instrument 1000 by measuring the magnetic field generated by said relative to the magnetic field source $MF_L$ (as indicated above both location and orientation may be determined). In this example, as shown in the figure three horizontal helical SMD-Coils 10H of the invention (only two are visible in the figure) and two vertical helical SMD-Coils 10V of the invention (only one is visible in the figure) are arranged in the sensor 100 over the folded/rolled flexible circuit board CB to provide a compact sensitive and reliable sensor configuration.

Figure 10A:
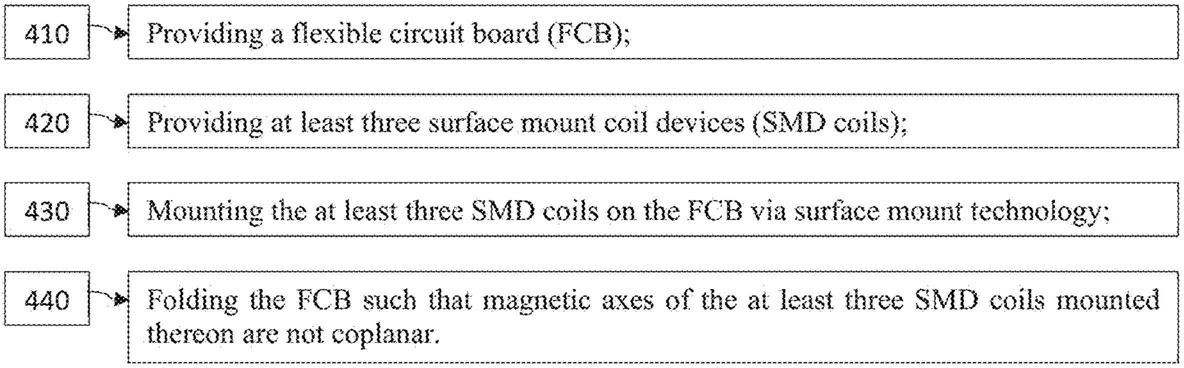
FIGS. 10A and 10B illustrate a method 400 to fabricate a magnetic position sensor according to an embodiment the present invention, whereby
Figure 10B:
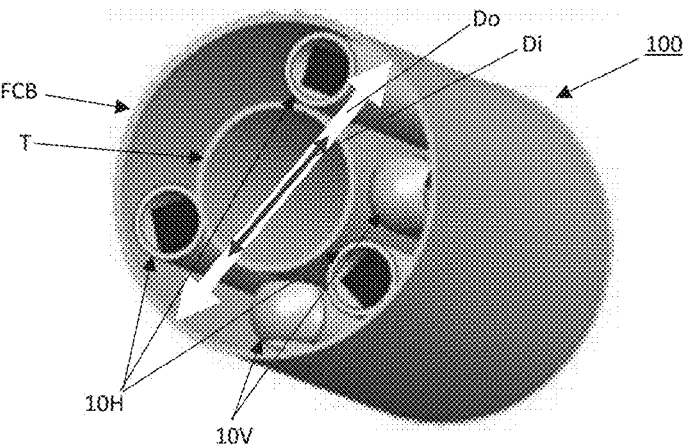

Reference is now made to FIGS. 10A and 10B. A method 400 to fabricate a magnetic position sensor 100 suitable for use in a medical instrument is schematically illustrated in a flow diagram in FIG. 10A. The method includes the following operations:

410—providing a flexible circuit board (FCB);

420—providing at least three surface mount coil devices (SMD coils);

430—mounting the at least three SMD coils on said FCB via surface mount technology; and

440—folding/rolling the FCB with the at least three SMD coils mounted thereon into tubular form whereby said folding is carried out such that magnetic axes of said at least three SMD coils are not coplanar thereby providing that magnetic fields sensed by said at least three SMD coils from one or more magnetic field sources enable measurement of at least one of a location and orientation of the sensor relative to the magnetic field sources.

More specifically, in operation 410, a flexible circuit board (FCB) is provided for mounting the coils of the magnetic position sensor thereon. The use of flexible circuit board (FCB) is advantageous over other techniques for connecting the coils, such as direct wiring, as it facilitates robust and accurate accommodation of the coils at proper locations and orientation on the sensor (e.g. in the medical device in which it resides), while also facilitating compact arrangement of the coils in cost effective manner. In operations 420 and 430, at least three surface mount coil devices (SMD coils) are provided and mounted on the FCB by using surface mount technology which facilitate accurate, compact and reliable/robust electrical and mechanical connection of the coils to the FCB. Then, in operation 440 the FCB is folded (e.g. rolled into tubular form with proper dimensions such that it can be fitted to the required diminutions of the sensor. For example, as indicated above in various implementations of the technique of the present invention the magnetic position sensor is to be fitted within a medical instrument, such as a catheter which has an elongated body/housing of tubular shape with characteristic diameter in the order of 2 millimeters. Accordingly, the FCB may be folded/rolled to have tubular/cylindrical form of smaller diameter which can be fitted in such medical instrument.

As indicated above in various implementations the FCB may be folded/rolled such that the SMD coils mounted thereon face inwardly and/or outwardly relative to the folding axis. The SMD coils are arranged on the FCB such that when the FCB is folded/rolled about a certain designated folding axis, the magnetic axes of the SMD coils are not coplanar with respect to one another to thereby facilitate measurement of at least one of a location and orientation of the sensor relative to one or more magnetic field sources. Several non-limiting examples of the mounting arrangement of the SMD coils on the FCB and the folding of the FCB therewith are illustrated for example in FIGS. 5A to 8C described above.

In some embodiments, as indicated above, the magnetic positioning sensor may be adapted to measure signals indicative of an orientation of the sensor relative to a magnetic field source (e.g. reference MFo in the figures described above). In such embodiments the mounting operation 430 may include mounting three of the SMD coils on the FCB such that their magnetic flux axes are parallel to one another and are not co-planar when the FCB is folded to the tubular form to thereby enable measurement of two angles of orientation the relative to the magnetic field source MFo when the latter is located in-front of the three SMD coils with respect to the general direction of their magnetic flux axes.

Alternatively or additionally, as also indicated above, the magnetic positioning sensor 10 may be adapted to measure signals indicative of location and orientation of the sensor relative to one or more external magnetic field sources (e.g. reference $MF_L$ in the figures described above). In such embodiments the mounting operation 430 may include mounting three of the SMD coils such that when the FCB is folded to the tubular form, their magnetic flux axes span 3D coordinates, and thereby enable measurement of the location and orientation of the sensor 100 relative to these one or more external magnetic field sources $MF_L$.

Yet alternatively or additionally in some implementations as exemplified for instance in FIG. 9C, the magnetic positioning sensor is adapted to measure signals indicative of an orientation of the sensor relative a first magnetic field source MFo and signals indicative of location and orientation of the sensor relative to one or more second external magnetic field sources $MF_L$. In such embodiments the at least three SMD coils provided in 420 include at least five SMD coils. In such embodiments the mounting in 430 is performed such that: a first subset of at least three of the SMD coils are arranged with their magnetic axes parallel to one another and such that after the FCB folding they remain parallel but not co-planar (to facilitate the orientation measurement relative to the first magnetic field source MFo as indicated above); a second subset of at least three of the SMD coils are arranged such that their magnetic flux axes span 3D coordinates after folding (operation 440) of the FCB (to facilitate the location and orientation measurement relative to the second magnetic field source(s) $MF_L$ as indicated above). Example of such arrangement of the coils is illustrated for instance in FIGS. 7A to 8C. As indicated above the mounting (operation 440) may be performed utilizing surface mount technology and may include mounting one or more of the SMD coils 10V with vertical orientation of their magnetic flux axes relative to the FCB surface and/or mounting one or more of the SMD coils 10H with horizontal/parallel orientation of their magnetic flux axes relative to the FCB surface.

In some embodiments in operation 440 the FCB with the SMD coils mounted thereon is folded/rolled to tubular form with sufficiently narrow outer diameter Do such that it can be fitted within a small/narrow medical instrument. For instance, in some implementations the outer diameter Do of the sensor Do after the FCB has been folded/rolled should not exceed about 2 millimeters. Thus, as illustrated schematically for instance in FIG. 10B in some embodiments a tube T may be used to assist proper folding of the FCB. The tube T may serve as an inner skeleton about which the FCB is folded as exemplified in FIG. 10B, or otherwise as an outer skeleton within which the folded FCB may be inserted. The tube T may be for example a polyimide tube. In the example illustrated in FIG. 10B the tube serves as an inner tube about which the FCB is folded and has a characteristic diameter Di of about 0.92 mm. The FCB is folded thereon to form an outer tube with diameter Do of 1.97 mm such that it can be fitted within the narrow medical instrument, and the SMD coils thus reside in the spacing (of about 0.53 mm) between the inner and outer diameters as shown in the figure. In some implementations the folding 440 further includes encapsulation (potting) of the electronic components (FCB, SMD coils etc.) of the sensor 100 together with any soldered cable wires connected thereto in order to form the sensor as a robust single piece unit. Sensor potting may be performed utilizing for instance UV or thermal adhesive and may be carried out in a single stage process or two-stage process (e.g. dam one end with adhesive, and then fill from the other end). Preferably during potting the empty spaces between the polyimide tube T and the rolled thin FCB with coils and any soldered cable wires connected thereto is filled with adhesive. Potting preferably also anchors any soldered cable wires connected to FCB/coils the cable in order to protect from mechanical stresses which may be applied thereto during insertion to the medical instrument.

It should be noted that in some embodiments, operation 420 of method 400 includes fabricating one or more of the SMD coils utilizing the method of the present invention as described above for instance in relation to FIG. 2 or FIG. 3. For instance, in certain embodiments the photolithographic coil fabrication technique described in relation to FIG. 2 is used in order to form one or more of the SMD coils with their helical coils directly on the ferrite core.

The invention claimed is:

1. A position sensor adapted to measure signals indicative of at least one of a location and orientation of the sensor, comprising:

a circuit board; and at least three coils located on said circuit board and arranged for sensing different aspects of an external magnetic field, which are indicative of at least one of a location and orientation of the sensor relative to one or more magnetic field sources;

characterized in that:

said circuit board is a flexible circuit board (FCB), and said at least three coils are at least three surface mount coil devices (SMD coils) mounted on the FCB via surface mount technology (SMT), each SMD coil comprising a core and a coil; and wherein said FCB is furnished at the sensor in a folded/rolled state such that magnetic flux axes of at least three of the SMD coils mounted on the surface of the FCB are not co-planar, thereby generating a plurality of signals from said at least three SMD coils, the plurality of signals being indicative of at least one of the orientation and location of the sensor relative to one or more magnetic field sources.

2. The position sensor according to claim 1 adapted to measure signals indicative of an orientation of the sensor relative to a first magnetic field source located in-front of the position sensor, wherein said at least three SMD coils include three SMD coils arranged on the FCB such that their magnetic flux axes are parallel to one another and are not co-planar when the FCB is furnished at the sensor in folded/rolled state; thereby enabling the signals obtained from said three SMD coils to be used to determine two angles of orientation of the position sensor relative to the first magnetic field source when it is being located in-front of the sensor with respect to a general direction of said magnetic flux axes.

3. The position sensor according to claim 2 wherein said three SMD coils are surface mounted to the surface of said FCB via surface mount technology with parallel orientation of their magnetic flux axes relative to the FCB surface; and wherein the FCB is arranged in folded/rolled form at the sensor such that a folding/rolling axis of said folded/rolled form is substantially parallel to the parallel magnetic flux axes of the three SMD coils thereon.

4. The position sensor according to claim 1, the position sensor being adapted to measure signals indicative of location and orientation of the sensor relative to one or more second magnetic field sources, wherein said at least three SMD coils include three SMD coils arranged on the FCB such that when the FCB is folded at the sensor, the magnetic flux axes of said three SMD coils span 3D coordinates, thereby enabling the signals obtained from said three SMD coils to be used to determine a location and orientation of the sensor relative to said one or more second magnetic field sources.

5. The position sensor according to claim 4 wherein two SMD coils of said three SMD coils are surface mounted to the surface of said FCB via surface mount technology with vertical orientation of their magnetic flux axes relative to the FCB surface such that when the FCB is furnished at the sensor in folded/rolled state, the magnetic flux axes of said two SMD coils are not parallel; and a third SMD coil of said three SMD coils is surface mounted to the surface of said FCB via surface mount technology with parallel orientation of its magnetic flux axis relative to the FCB surface.

6. The position sensor according to claim 1, wherein said at least three SMD coils include at least five SMD coils surface mounted to one or more FCBs of said sensor, wherein a first subset of said at least five SMD coils comprises three SMD coils arranged such that their magnetic flux axes are parallel to one another and are not co-planar when the FCB is furnished at the sensor in folded/rolled state, thereby enabling the signals obtained from the three SMD coils of said first subset to be used to determine two angles of orientation of the sensor relative to a first magnetic field source located in-front of the three SMD coils along a general direction of their magnetic flux axes; and wherein a second subset of said at least five SMD coils comprises three SMD coils arranged such that when the FCB is furnished at the sensor in folded/rolled state, their magnetic flux axes span 3D coordinates, thereby enabling the signals obtained from the three SMD coils of said second subset to be used to determine a location and orientation of the sensor relative to one or more external second magnetic field sources.

7. The position sensor according to claim 1, wherein at least one SMD coil of the at least three SMD coils comprises a coil portion and at least one surface mount portion arranged from at least one respective side of the coil portion;

whereby the coil portion comprises a ferrite core and a conductive winding arrangement arranged in a helix directly over an external surface of said ferrite core with a pitch of said helix not exceeding 12-13 μm.

8. The position sensor according to claim 7, wherein said ferrite core comprises material of relative magnetic permeability $\mu_r$ in the order of at least 100 and wherein the relative magnetic permeability of said material of the ferrite core is stable with tolerance of +0.3% within a temperature range between about 20° C. to 60° C. to enable consistent magnetic field measurements during operation under variable temperature conditions within said temperature range.

9. The position sensor according to claim 7, wherein said conductive winding arrangement is fabricated utilizing photolithography directly over said external surface of the ferrite core.

10. The position sensor according to claim 1, wherein at least one SMD coil of the at least three SMD coils is mounted in a flat/parallel orientation of its magnetic flux axis relative to the FCB surface and includes a coil portion having a conductive winding arrangement and at least two SMT-mounting portions arranged from opposite sides of the coil portion and having at least two respective electric contacts electrically coupled to the FCB with SMT electrical connection and respectively electrically connected to opposite ends of the conductive winding arrangement.

11. The position sensor according to claim 1, wherein at least one SMD coil of the at least three SMD coils is mounted in a vertical/perpendicular orientation of its magnetic flux axis relative to the FCB surface and includes a coil portion having a conductive winding arrangement and at least one SMT-mounting portion arranged from at least one side of the coil portion and having at least two electric contacts electrically coupled to the FCB via SMT electrical connection and respectively electrically connected to opposite ends of the conductive winding arrangement.

12. A medical instrument comprising a position sensor configured according to claim 1.

13. A medical instrument according to claim 12, wherein said medical instrument is a catheter having an elongated housing comprising a main section having a longitudinal axis and a tip section that is flexibly coupled to a distal end of the main section and includes a first magnetic field source, wherein said position sensor is accommodated at the main section of the elongated housing such that said FCB being folded/rolled about an axis parallel to said longitudinal axis; a first subset facilitates determining an orientation of said tip section relative to the main section of the housing based on measurement of magnetic fields from said first magnetic field source and a second subset facilitates determining a location and orientation of said main section relative to one or more external second magnetic field sources.

14. A method to fabricate a magnetic position sensor suitable for use in a medical instrument comprising:

providing a flexible circuit board (FCB);

providing at least three surface mount coil devices (SMD coils), each SMD coil comprising a core and a coil;

mounting the at least three SMD coils on said FCB via surface mount technology (SMT);

folding said FCB with said at least three SMD coils into tubular form whereby said folding is carried out such that a magnetic axes of each of said at least three SMD coils are not coplanar with respect to one another, such that magnetic fields sensed by said at least three SMD coils from one or more magnetic field sources are indicative of at least one of a location and orientation of the sensor relative to said sources.

15. The method according to claim 14, wherein said medical instrument is a catheter having a body of tubular shape with an inner diameter of about 2.5 millimeters or less, and wherein said folding is carried out such that a diameter of said FCB after being folded is smaller than the inner diameter of the body of the catheter, the method further including placing the folded FCB within said body.

16. The method according to claim 14, wherein the magnetic position sensor is adapted to measure signals indicative of an orientation of the sensor relative to a magnetic field source; said mounting of the at least three SMD coils comprises mounting three of the SMD coils on the FCB such that their magnetic flux axes are parallel to one another and are not co-planar when the FCB is folded to said tubular form, thereby enabling the signals obtained from said three SMD coils to be used to determine two angles of orientation relative to a magnetic field source located in-front of the three SMD coils along a general direction of their magnetic flux axes.

17. The method according to claim 14, wherein the magnetic position sensor is adapted to measure signals indicative of location and orientation of the sensor relative to one or more external magnetic field sources, and wherein said mounting of the at least three SMD coils comprises mounting three of the SMD coils on the FCB such that when the FCB is folded to said tubular form, the magnetic flux axes of said three SMD coils span 3D coordinates, thereby enabling the signals obtained from said three SMD coils to be used to determine location and orientation of the sensor relative the external magnetic field sources.

18. The method according to claim 14, wherein the magnetic position sensor is adapted to measure signals indicative of an orientation of the sensor relative to a first magnetic field source and signals indicative of location and orientation of the sensor relative to one or more second external magnetic field sources;

said at least three SMD coils include at least five SMD coils, and wherein said mounting comprises mounting said at least five SMD coils such that the following arrangement of magnetic flux axes thereof is obtained when the FCB is folded to said tubular form:

the magnetic flux axes of a first subset, which includes at least three SMD coils of said at least five SMD coils, are parallel to one another and are not co-planar to facilitate utilization of signals obtained from said first subset to determine two angles of orientation relative to said first magnetic field source when being located in-front of the three SMD coils of the first subset along a general direction of their parallel magnetic flux axes;

the magnetic flux axes of a second subset, which includes at least three SMD coils of said at least five SMD coils, span 3D coordinates to facilitate utilization of signals obtained from said first subset to determine location and orientation of the sensor relative the one or more external magnetic field sources.

19. The method according to claim 14, wherein said mounting is performed utilizing surface mount technology and comprises at least one of the following:

mounting two SMD coils with vertical orientation of their magnetic flux axes relative to the FCB surface and one SMD coil with parallel orientation of its magnetic flux axis relative to the FCB surface such that when the FCB is in folded state, the magnetic flux axes of said two SMD coils and said one SMD coil span 3D coordinates; and mounting three SMD coils with parallel orientation of their magnetic flux axes relative to the FCB surface such that when the FCB is folded about an axis parallel to the magnetic flux axes, the magnetic flux axes of said three SMD coils are parallel and not co-planar.

20. The method according to claim 14, wherein said providing of the at least three SMD coils comprises fabricating at least one SMD coil of said SMD coils utilizing a photolithographic method to form helical conductive windings directly on a ferrite core, wherein the photolithographic method comprises:

applying a photoresist layer to cover at least a tubular section of the ferrite core;

applying photolithography to pattern the photoresist layer to form a helical pattern over the tubular section covered by said photoresist layer; and electroplating an external surface layer of said ferrite core at the exposed regions of said helical pattern to form said conductive helical windings directly on an external surface layer of said tubular section the ferrite core.

21. The method according to claim 20 wherein:

said photolithographic method is adapted for fabrication of high density conductive helical windings, and wherein a pitch of said helical pattern and correspondingly of said conductive helical windings is in the order of, or less than, 10 μm; or said ferrite core comprises fully sintered magnetic material having relative magnetic permeability $\mu_r$ in the order of at least 100; and wherein said photolithography utilizes a photolithographic light source providing light power density (LDP) and wavelength suited for patterning said photoresists while not inducing substantial damage to the ferrite core; or said applying of the photoresist layer comprises applying a layer of dry photoresist with thickness of at least 8 μm to enable said electroplating to yield narrow line width of said helical conductive windings with small pitch between adjacent lines and prevent spread electroplating between them; or prior to said electroplating, said photolithographic method comprises fabricating a seed layer over at least a section of the ferrite core to increase a surface conductivity of the ferrite and facilitate said electroplating; or after said electroplating, said photolithographic method comprises removing remaining photoresists material from between conductive helical windings; or said ferrite core is provided with at least one surface mount portion arranged from at least one respective side thereof; and said photoresist, photolithography and electroplating are applied to also form one or more conductive couplings between at least one end of said conductive helical windings and one or more designated locations on said at least one surface mount portion to form one or more SMT contacts.

* * * * *